(12) United States Patent
Pirrung et al.

(10) Patent No.: US 10,584,105 B2
(45) Date of Patent: Mar. 10, 2020

(54) IMMUNOPROTEASOME INHIBITOR ANALOGS

(71) Applicants: The Regents of the University of California, Oakland, CA (US); Board of Trustees of Michigan State University, East Lansing, MI (US)

(72) Inventors: Michael C. Pirrung, Riverside, CA (US); Nicole A. Bakas, Victorville, CA (US); Andre Bachmann, Grand Rapids, MI (US)

(73) Assignees: The Regents of the University of California, Oakland, CA (US); Board of Trustees of the Michigan State University, East Lansing, MI (US)

( * ) Notice: Subject to any disclaimer, the term of this patent is extended or adjusted under 35 U.S.C. 154(b) by 0 days.

(21) Appl. No.: 16/078,348

(22) PCT Filed: Mar. 10, 2017

(86) PCT No.: PCT/US2017/021931
§ 371 (c)(1),
(2) Date: Aug. 21, 2018

(87) PCT Pub. No.: WO2017/156471
PCT Pub. Date: Sep. 14, 2017

(65) Prior Publication Data
US 2019/0047969 A1 Feb. 14, 2019

Related U.S. Application Data

(60) Provisional application No. 62/307,370, filed on Mar. 11, 2016, provisional application No. 62/307,433, filed on Mar. 12, 2016.

(51) Int. Cl.
| C07D 281/00 | (2006.01) |
| C07D 285/00 | (2006.01) |
| C07D 417/12 | (2006.01) |
| A61K 45/06 | (2006.01) |
| C07K 5/062 | (2006.01) |
| A61P 35/00 | (2006.01) |
| A61K 9/00 | (2006.01) |
| A61K 31/395 | (2006.01) |
| A61K 31/497 | (2006.01) |

(52) U.S. Cl.
CPC .......... *C07D 281/00* (2013.01); *A61K 9/0019* (2013.01); *A61K 31/395* (2013.01); *A61K 31/497* (2013.01); *A61K 45/06* (2013.01); *A61P 35/00* (2018.01); *C07D 285/00* (2013.01); *C07D 417/12* (2013.01); *C07K 5/06052* (2013.01)

(58) Field of Classification Search
CPC ... C07D 281/00; C07D 285/00; C07D 417/12
See application file for complete search history.

(56) References Cited

U.S. PATENT DOCUMENTS

| 2013/0065872 A1 | 3/2013 | Pirrung |
| 2015/0336915 A1 | 11/2015 | Engelking et al. |

FOREIGN PATENT DOCUMENTS

| EP | 2210881 A1 | 7/2010 |
| WO | 2013/188750 A2 | 12/2013 |
| WO | 2014/183015 A1 | 11/2014 |
| WO | 2016/014551 A1 | 1/2016 |

OTHER PUBLICATIONS

Thomas, Shane, International Search Report and Written Opinion, PCT/US17/21931, dated May 25, 2017.
Bakas, N.A. et al., "Immunoproteasome inhibition and bioactivity of thiasyrbactins", Bioorganic & Medicinal Chemistry, vol. 26, No. 2, Dec. 7, 2017, pp. 401-412.
Clerc, J. et al., "Synthetic and structural studies on syringolin A and B reveal critical determinants of selectivity and potency of proteasome inhibition", PNAS, National Academy of Sciences, vol. 106, No. 16, 2009, pp. 6507-6512.
Ibarra-Rivera, T.R. et al., "Syntheses and cytotoxicity of syringolin B-based proteasome inhibitors", Tetrahedron, vol. 67, No. 51, 2011, pp. 9950-9956.
Kiernan, Andrea, Supplementary European Search Report, European Patent Office, Application No. 17764239.4, dated Sep. 4, 2019.
Ogorevc, E. et al., "A patent review of immunoproteasome inhibitors", Expert Opinion on Therapeutic Patents, vol. 28, No. 7, Jun. 14, 2018, pp. 517-540.
Wittmann-Regis, Agnes, International Preliminary Report on Patentability and Written Opinion, PCT/US17/21931, dated Sep. 20, 2018.

*Primary Examiner* — Rebecca L Anderson
(74) *Attorney, Agent, or Firm* — Gavrilovich, Dodd & Lindsey LLP

(57) ABSTRACT

The disclosure provides for compounds having immunoproteasome inhibitory activity, and pharmaceutical compositions made thereof. The disclosure further provides for the use of the compounds and compositions in treating various diseases and disorders in a subject that are associated with immunoproteasome activity, including inflammatory disorders, autoimmune disorders, hematological disorders, and neurodegenerative disorders.

20 Claims, 8 Drawing Sheets

NAM - 105
Chemical Formula: $C_{28}H_{51}N_5O_4S$
Molecular Weight: 553.8070

NAM - 135
Chemical Formula: $C_{28}H_{51}N_5O_5S$
Molecular Weight: 569.8060

NAM - 95
Chemical Formula: $C_{20}H_{28}N_6O_4S$
Molecular Weight: 448.5420

NAM - 93
Chemical Formula: $C_{28}H_{42}N_4O_4S$
Molecular Weight: 530.7280

NAM - 41
Chemical Formula: $C_{15}H_{19}N_5O_3S$
Molecular Weight: 349.4090

NAM - 111
Chemical Formula: $C_{15}H_{19}N_5O_4S$
Molecular Weight: 365.4080

IMMUNOPROTEASOME INHIBITOR ANALOGS

CROSS REFERENCE TO RELATED APPLICATIONS

This application is a U.S. National Stage Application filed under 35 U.S.C. § 371 and claims priority to International Application No. PCT/US2017/021931, filed Mar. 10, 2017, which application claims priority under 35 U.S.C. § 119 from Provisional Application Ser. No. 62/307,370, filed Mar. 11, 2016 and from Provisional Application Ser. No. 62/307,433, filed Mar. 12, 2016, the disclosures of which are incorporated herein by reference.

TECHNICAL FIELD

The disclosure provides for compounds having immunoproteasome inhibitory activity, and pharmaceutical compositions made thereof. The disclosure further provides for the use of the compounds and compositions in treating various diseases and disorders in a subject that are associated with immunoproteasome activity, including inflammatory disorders, autoimmune disorders, hematological disorders, and neurodegenerative disorders.

BACKGROUND

The syringolin and glidobactin natural products are irreversible inhibitors of the proteasome. Proteasome inhibitors have been shown to exert beneficial biological effects when administered to subjects.

SUMMARY

The disclosure provides for compounds having immunoproteasome inhibitory activity. In particular, the compounds disclosed herein inhibit the immunoproteasome trypsin-like catalytic activity, which historically has been very difficult to target with a drug compound (e.g., see FIG. 1).

In a particular embodiment, the disclosure provides for a compound comprising a structure of Formula I:

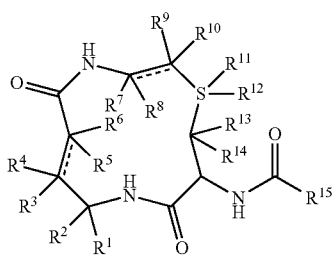

Formula I or a pharmaceutically acceptable salt, or solvate thereof, wherein, $R^1$ and $R^2$ are independently selected from the group consisting of H, cyano, an optionally substituted $(C_1-C_6)$alkyl and an optionally substituted cycloalkyl; $R^3-R^{10}$, $R^{13}$ and $R^{14}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanate, isocyanato, an optionally substituted $(C_1-C_6)$alkyl, an optionally substituted $(C_2-C_6)$alkenyl, an optionally substituted $(C_2-C_6)$alkynyl, an optionally substituted $(C_1-C_6)$hetero-alkyl, an optionally substituted $(C_2-C_6)$hetero-alkenyl, an optionally substituted $(C_2-C_6)$hetero-alkynyl, an optionally substituted $(C_3-C_8)$cycloalkyl, an optionally substituted aryl, and an optionally substituted heterocycle; $R^{11}$ and $R^{12}$ are independently selected from H, =O, and an optionally substituted $(C_1-C_6)$alkyl, wherein $R^{11}$ and/or $R^{12}$ may also be absent; $R^{15}$ is selected from the group consisting of

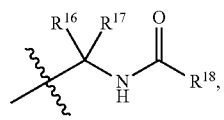

an optionally substituted heterocycle, an optionally substituted aryl, an optionally substituted benzyl, and an optionally substituted $(C_3-C_8)$cycloalkyl, $—CH_2(R^{19})$, $—CH(R^{19})_2$, $—NH(R^{19})$ and $—N(R^{19})_2$; $R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_6)$alkyl, an optionally substituted $(C_2-C_6)$alkenyl, an optionally substituted $(C_2-C_6)$alkynyl, an optionally substituted $(C_1-C_6)$hetero-alkyl, an optionally substituted $(C_2-C_6)$hetero-alkenyl, an optionally substituted $(C_2-C_6)$hetero-alkynyl, an optionally substituted $(C_3-C_8)$cycloalkyl, an optionally substituted aryl, and an optionally substituted heterocycle; $R^{18}$ is selected from the group consisting of $—CH_2(R^{19})$, $—CH(R^{19})_2$, $—NH(R^{19})$, $—N(R^{19})_2$, an optionally substituted heterocycle, an optionally substituted aryl, an optionally substituted benzyl, and an optionally substituted $(C_3-C_8)$cycloalkyl; and $R^{19}$ is selected from the group consisting of an optionally substituted $(C_3-C_{16})$ alkyl, an optionally substituted $(C_3-C_{16})$alkenyl, an optionally substituted $(C_3-C_{16})$alkynyl, an optionally substituted $(C_3-C_{15})$hetero-alkyl, an optionally substituted $(C_3-C_{15})$hetero-alkenyl, an optionally substituted $(C_3-C_{15})$hetero-alkynyl, an optionally substituted heterocycle, an optionally substituted aryl, an optionally substituted benzyl, and an optionally substituted $(C_3-C_8)$cycloalkyl. In a further embodiment, the disclosure provides for a compound having the structure of Formula II:

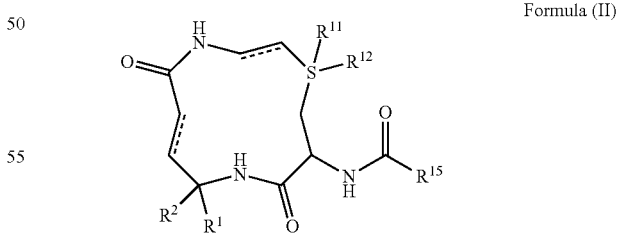

Formula (II)

or a pharmaceutically acceptable salt, or solvate thereof, wherein, $R^1$ and $R^2$ are independently selected from the group consisting of H, cyano, an optionally substituted $(C_1-C_6)$alkyl and an optionally substituted cycloalkyl; $R^{11}$ and $R^{12}$ are independently selected from H, =O, and an optionally substituted $(C_1-C_6)$alkyl, wherein $R^{11}$ and/or $R^{12}$ may also be absent; $R^{15}$ is selected from the group consisting of

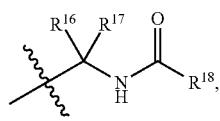

an optionally substituted heterocycle, an optionally substituted aryl, an optionally substituted benzyl, and an optionally substituted $(C_3-C_8)$cycloalkyl, —$CH_2(R^{19})$, —$CH(R^{19})_2$, —$NH(R^{19})$ and —$N(R^{19})_2$; $R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_6)$alkyl, an optionally substituted $(C_2-C_6)$alkenyl, an optionally substituted $(C_2-C_6)$alkynyl, an optionally substituted $(C_1-C_6)$hetero-alkyl, an optionally substituted $(C_2-C_6)$hetero-alkenyl, an optionally substituted $(C_2-C_6)$hetero-alkynyl, an optionally substituted $(C_3-C_8)$cycloalkyl, an optionally substituted aryl, and an optionally substituted heterocycle; $R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted $(C_3-C_8)$cycloalkyl; and $R^{19}$ is selected from the group consisting of an optionally substituted $(C_3-C_{16})$ alkyl, an optionally substituted $(C_3-C_{16})$alkenyl, an optionally substituted $(C_3-C_{16})$alkynyl, an optionally substituted $(C_3-C_{15})$hetero-alkyl, an optionally substituted $(C_3-C_{15})$hetero-alkenyl, an optionally substituted $(C_3-C_{15})$hetero-alkynyl, an optionally substituted heterocycle, an optionally substituted aryl, an optionally substituted benzyl, and an optionally substituted $(C_3-C_8)$cycloalkyl. In a further embodiment, the disclosure provides for a compound which comprises the structure of Formula II(a):

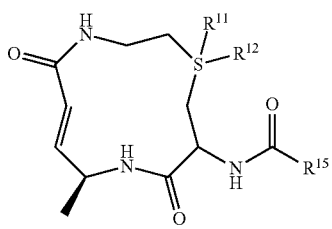

Formula II(a)

or a pharmaceutically acceptable salt, or solvate thereof, wherein, $R^{11}$ and $R^{12}$ are independently selected from H, =O, and an optional substituted $(C_1-C_6)$alkyl, or wherein $R^{11}$ and/or $R^{12}$ may also be absent; $R^{15}$ is selected from the group consisting of

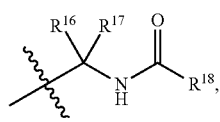

an optionally substituted heterocycle, an optionally substituted aryl, an optionally substituted benzyl, and an optionally substituted $(C_3-C_8)$cycloalkyl, —$CH_2(R^{19})$, —$CH(R^{19})_2$, —$NH(R^{19})$ and —$N(R^{19})_2$; $R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_6)$alkyl, an optionally substituted $(C_2-C_6)$alkenyl, an optionally substituted $(C_2-C_6)$alkynyl, an optionally substituted $(C_1-C_6)$hetero-alkyl, an optionally substituted $(C_2-C_6)$hetero-alkenyl, an optionally substituted $(C_2-C_6)$hetero-alkynyl, an optionally substituted $(C_3-C_8)$cycloalkyl, an optionally substituted aryl, and an optionally substituted heterocycle; $R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted $(C_3-C_8)$cycloalkyl; and $R^{19}$ is selected from the group consisting an optionally substituted $(C_3-C_{16})$ alkyl, an optionally substituted $(C_3-C_{16})$alkenyl, an optionally substituted $(C_3-C_{16})$alkynyl, an optionally substituted $(C_3-C_{15})$hetero-alkyl, an optionally substituted $(C_3-C_{15})$hetero-alkenyl, an optionally substituted $(C_3-C_{15})$hetero-alkynyl, an optionally substituted heterocycle, an optionally substituted aryl, an optionally substituted benzyl, and an optionally substituted $(C_3-C_8)$cycloalkyl. In another embodiment, the disclosure provides for a compound which comprises the structure of Formula II(b):

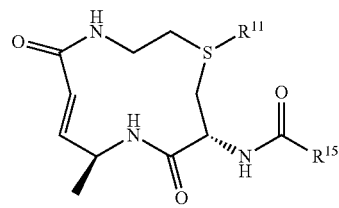

Formula II(b)

or a pharmaceutically acceptable salt, or solvate thereof, wherein, $R^{11}$ is =O or is absent; $R^{15}$ is selected from the group consisting of

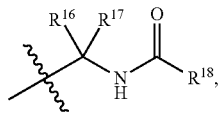

an optionally substituted heterocycle, an optionally substituted aryl, an optionally substituted benzyl, and an optionally substituted $(C_3-C_8)$cycloalkyl, —$CH_2(R^{19})$, —$CH(R^{19})_2$, —$NH(R^{19})$ and —$N(R^{19})_2$; $R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_6)$alkyl, an optionally substituted $(C_2-C_6)$alkenyl, an optionally substituted $(C_2-C_6)$alkynyl, an optionally substituted $(C_1-C_6)$hetero-alkyl, an optionally substituted $(C_2-C_6)$hetero-alkenyl, an optionally substituted $(C_2-C_6)$hetero-alkynyl, an optionally substituted $(C_3-C_8)$cycloalkyl, an optionally substituted aryl, and an optionally substituted heterocycle; $R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted $(C_3-C_8)$cycloalkyl; and $R^{19}$ is selected from the group consisting of an optionally substituted $(C_3-C_{16})$ alkyl, an optionally substituted $(C_3-C_{16})$alkenyl, an optionally substituted $(C_3-C_{16})$alkynyl, an optionally substituted $(C_3-C_{15})$hetero-alkyl, an optionally substituted $(C_3-C_{15})$hetero-alkenyl, an optionally substituted $(C_3-C_{15})$hetero-alkynyl, an optionally substituted heterocycle, an optionally substituted aryl, an optionally substituted benzyl, and an optionally substituted $(C_3-C_8)$cycloalkyl. In a further embodiment, for a compound disclosed herein, $R^{15}$ is selected from the group consisting of:

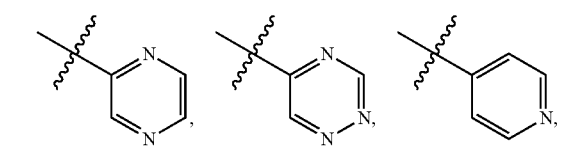

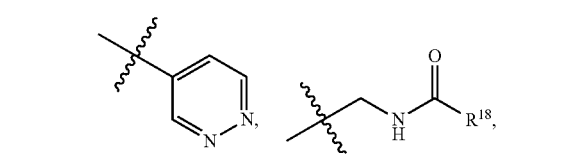

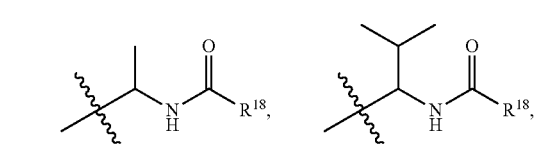

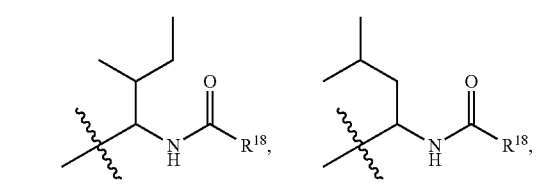

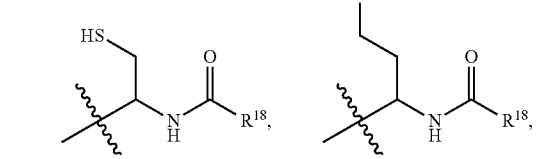

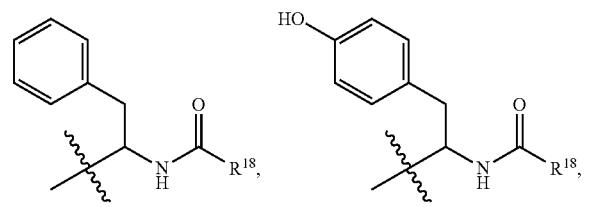

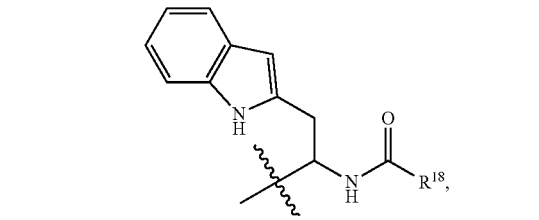

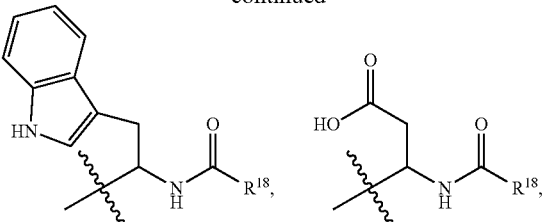

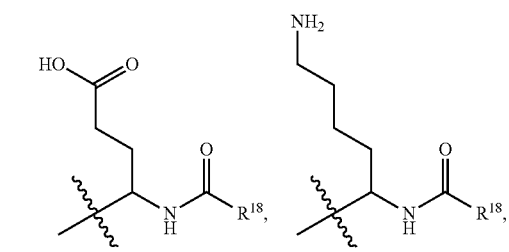

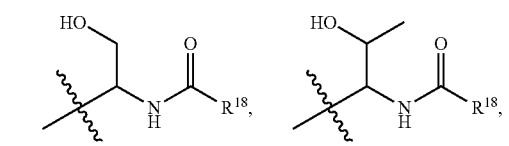

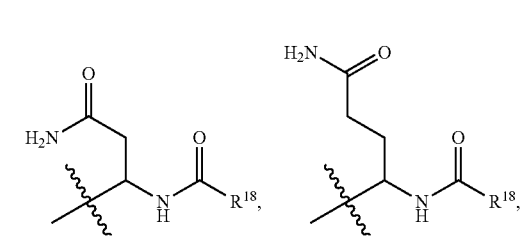

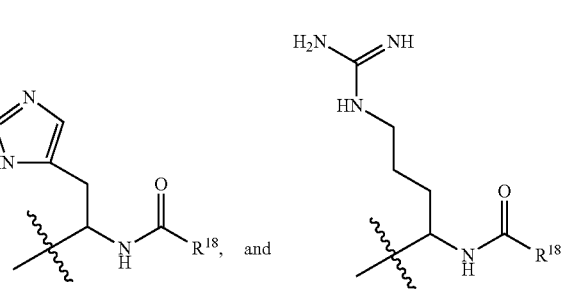

wherein, $R^{18}$ is selected from the group consisting of —CH$_2$(R$^{19}$), —CH(R$^{19}$)$_2$, —NH(R$^{19}$), —N(R$^{19}$)$_2$, an optionally substituted heterocycle, an optionally substituted aryl, an optionally substituted benzyl, and an optionally substituted $(C_3-C_8)$cycloalkyl; and $R^{19}$ is selected from the group consisting an optionally substituted $(C_3-C_{16})$ alkyl, an optionally substituted $(C_3-C_{16})$alkenyl, an optionally substituted $(C_3-C_{16})$alkynyl, an optionally substituted $(C_3-C_{15})$hetero-alkyl, an optionally substituted $(C_3-C_{15})$hetero-alkenyl, an optionally substituted $(C_3-C_{15})$hetero-alkynyl, an optionally substituted heterocycle, an optionally substituted aryl, an optionally substituted benzyl, and an optionally substituted $(C_3-C_8)$cycloalkyl. In yet a further embodiment, the disclosure provides for a compound which comprises the structure of Formula III:

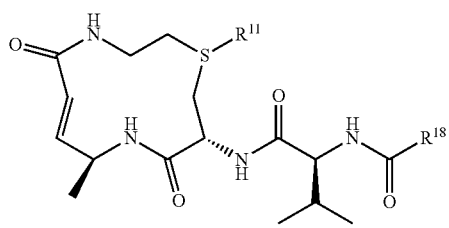

Formula III or a pharmaceutically acceptable salt, or solvate thereof, wherein, $R^{11}$ is =O or is absent; $R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted ($C_3$-$C_8$)cycloalkyl; and $R^{19}$ is selected from the group consisting an optionally substituted ($C_3$-$C_{16}$) alkyl, an optionally substituted ($C_3$-$C_{16}$)alkenyl, an optionally substituted ($C_3$-$C_{16}$)alkynyl, an optionally substituted ($C_3$-$C_{15}$)hetero-alkyl, an optionally substituted ($C_3$-$C_{15}$)hetero-alkenyl, an optionally substituted ($C_3$-$C_{15}$)hetero-alkynyl, an optionally substituted heterocycle, an optionally substituted aryl, an optionally substituted benzyl, and an optionally substituted ($C_3$-$C_8$)cycloalkyl. In yet another embodiment, for a compound disclosed herein, $R^{18}$ is selected from the group consisting of: octanyl, nonanyl, decanyl, undecanyl, dodecanyl, tridecanyl, tetradecanyl, pentadecanyl, hexadecanyl, benzene, phenol, toluene, ethyl benzene, p-xylene, m-xylene, mesitylene, durene, 2-phyenylhexane, biphenyl, aniline, nitrobenzene, benzoic acid, naphthalene, anthracene, phenanthrene, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, quinolizidine and 1-ethyl-4-isobutylbenzene. In a further embodiment, for a compound disclosed herein, $R^{19}$ is selected from the group consisting of: octanyl, nonanyl, decanyl, undecanyl, dodecanyl, benzene, phenol, toluene, ethyl benzene, p-xylene, m-xylene, mesitylene, durene, 2-phyenylhexane, biphenyl, aniline, nitrobenzene, benzoic acid, naphthalene, anthracene, phenanthrene, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydropyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, hexamethylene oxide, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, quinolizidine and 1-ethyl-4-isobutylbenzene. In a certain embodiment, the disclosure provides for a compound which comprises the structure of:

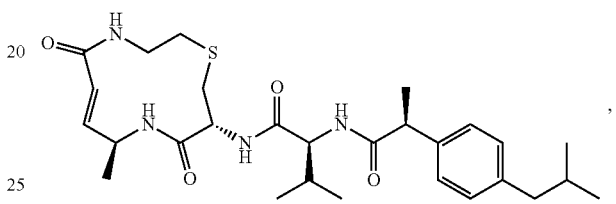

or a pharmaceutically acceptable salt, or solvate thereof. In an alternate embodiment, the disclosure provides for a compound with the structure of:

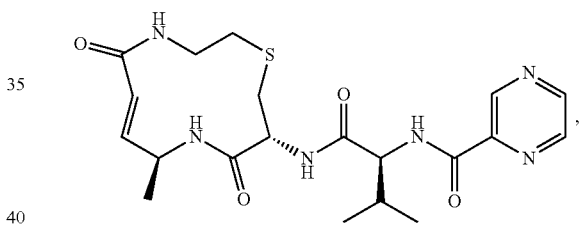

or a pharmaceutically acceptable salt, or solvate thereof. In another alternate embodiment, the disclosure provides for a compound with the structure of:

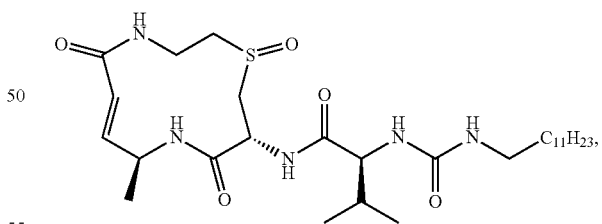

or a pharmaceutically acceptable salt, or solvate thereof.

In yet a particular embodiment, the disclosure also provides for a pharmaceutical composition comprising a compound disclosed herein and a pharmaceutically acceptable carrier. In a further embodiment, the composition is formulated to be administered intravenously, or subcutaneously.

In a certain embodiment, the disclosure further provides a method of treating a subject having or suspected of having an immunoproteasome mediated disorder comprising administering any one of the compounds disclosed herein, or a pharmaceutical composition of the disclosure. In a further embodiment, the immunoproteasome mediated disorder is selected from the group consisting of an inflammatory disease, an autoimmune disease, obesity, and a metabolic disorder. Examples of inflammatory diseases, include but are not limited to, colitis, asthma, inflammatory bowel disease, Crohn's disease, ulcerative colitis, Alzheimer's disease, and Nakajo-Nishimura syndrome. Examples of autoimmune diseases, include but are not limited to, autoimmune encephalomyelitis, thyroiditis, rheumatoid arthritis, multiple sclerosis, systemic lupus erythematosus, Sjögren's syndrome, celiac sprue disease, pernicious anemia, vitiligo, scleroderma, psoriasis, Hashimoto's disease, Addison's disease, Graves' disease, and type 1 diabetes. Examples of metabolic disorder, includes but are not limited to, dyslipidemia and hyperglycemia. In another embodiment, the immunoproteasome mediated disorder is a hematological malignancy. Examples of hematological malignancies, include but are not limited to, multiple myeloma or mantle cell lymphoma. In a further embodiment, the method further comprises administering of one or more additional therapeutic agents. Examples of such agents include but are not limited to, chemotherapeutic agents, proteasome inhibitors, and immunomodulators.

DETAILED DESCRIPTION

Figure 1:
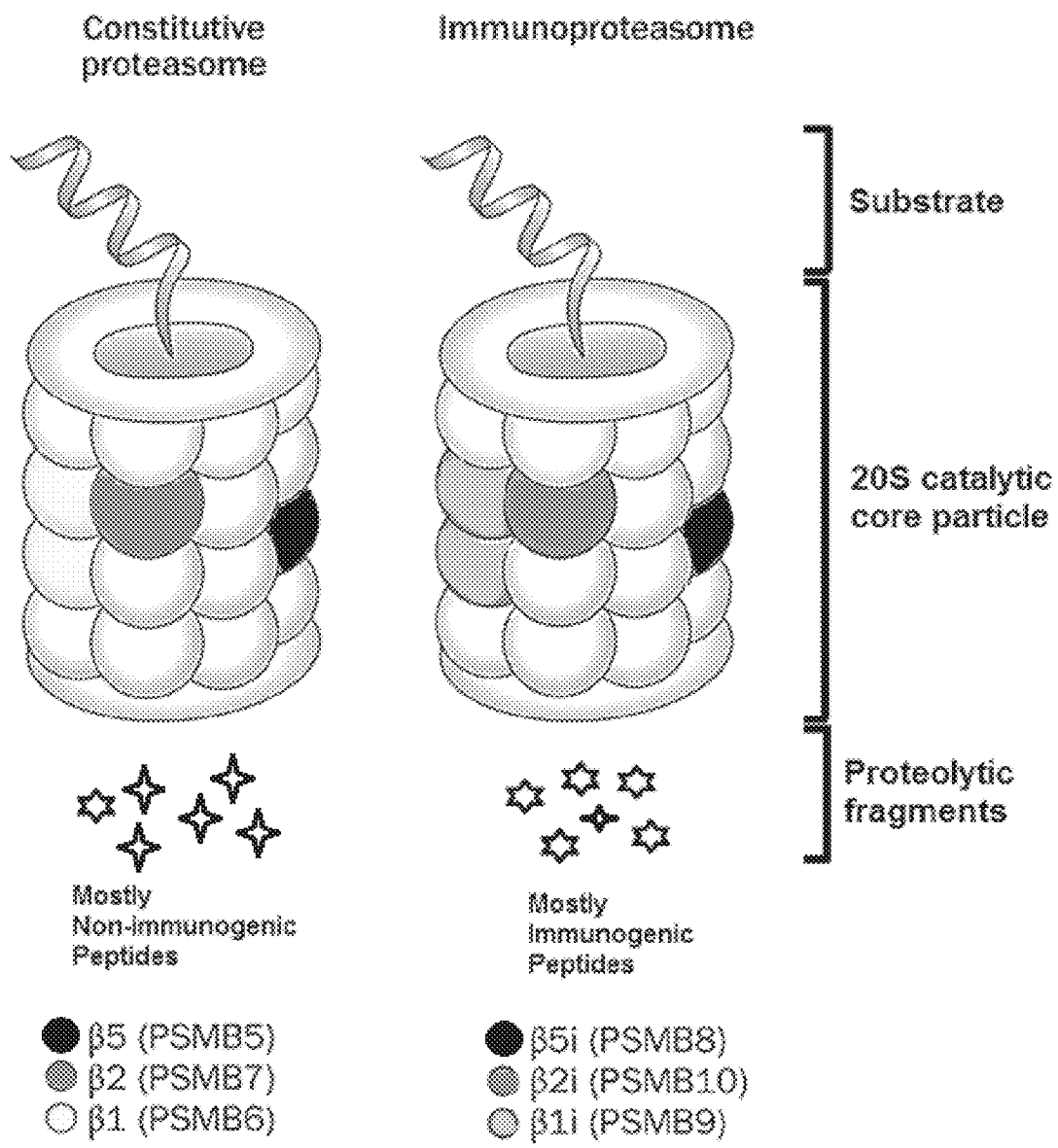
FIG. 1 provides a diagram of the components making up the constitutive proteasome and the immunoproteasome, including indicating the difference in peptides formed by each.
Figure 2:
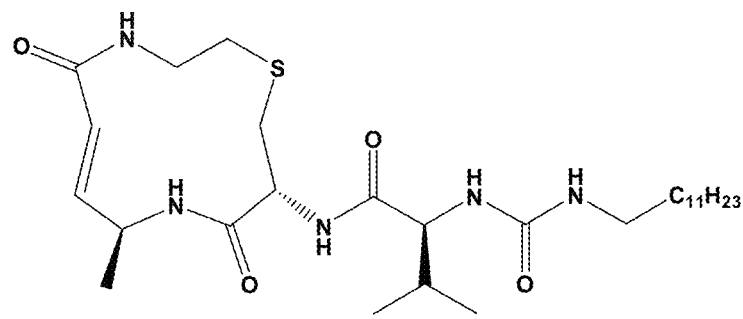
FIG. 2 presents a sampling of exemplary compounds of the disclosure.
Figure 2:
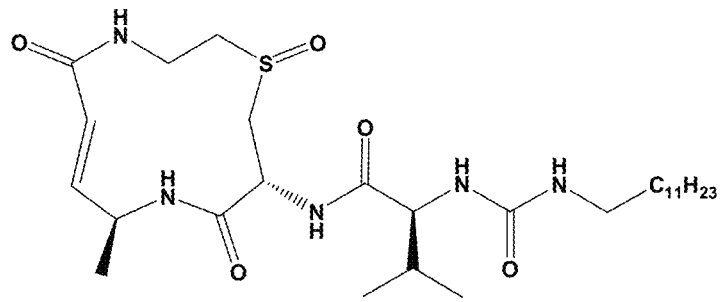
Figure 2:
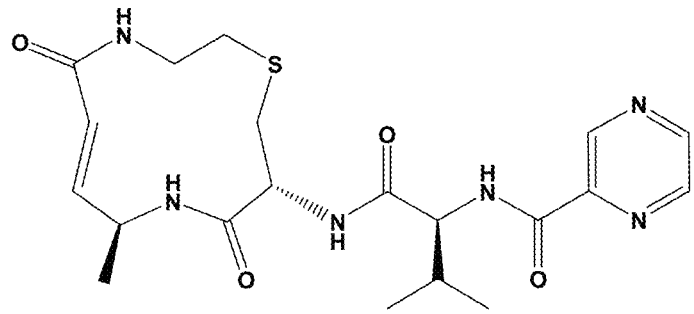
Figure 2:
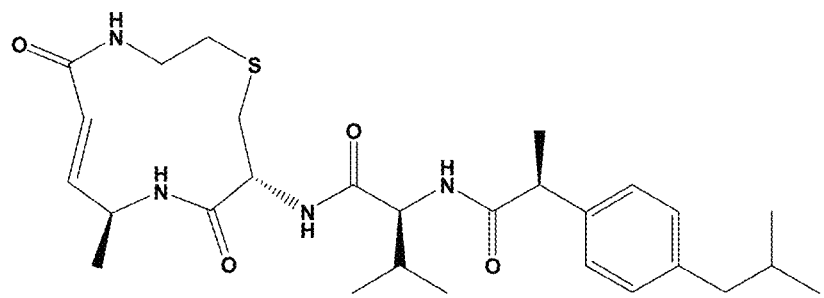
Figure 2:
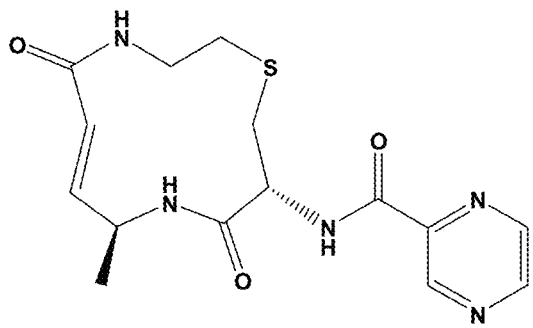
Figure 2:
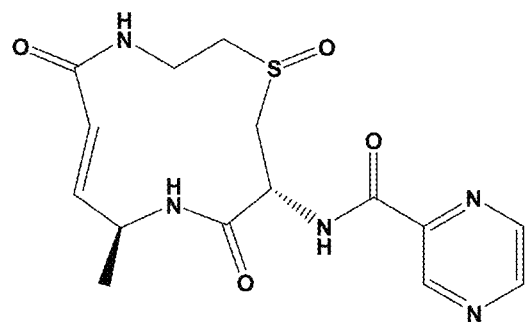

As used herein and in the appended claims, the singular forms "a," "an," and "the" include plural referents unless the context clearly dictates otherwise. Thus, for example, reference to "an immunoproteasome" includes a plurality of such immunoproteasomes and reference to "the therapeutic agent" includes reference to one or more therapeutic agents and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although there are many methods and reagents similar to or equivalent to those described herein, the exemplary methods and materials are presented herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

The terms "active ingredient," "active compound," and "active substance" as used herein, refers to a compound that when administered, alone or in combination with one or more pharmaceutically acceptable excipients or carriers, exerts or induces a physiological effect in a subject. Generally, an active ingredient can be administered to a subject to treat, prevent, or ameliorate one or more symptoms of a disease or disorder.

The term "alkenyl", refers to an organic group that is comprised of carbon and hydrogen atoms that contains at least one double covalent bond between two carbons. Typically, an "alkenyl" as used in this disclosure, refers to organic group that contains 2, 3, 4, 5, 6, 7, 8, 9, 10, 11, 12, 13, 14, 15, 16, 17, 18, 19, 20, or 30 carbon atoms, or a range of carbon atoms from any two of the foregoing numbers, unless stated otherwise. While a $C_2$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 2 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkyl", refers to an organic group that is comprised of carbon and hydrogen atoms that contains single covalent bonds between carbons. Typically, an "alkyl" as used in this disclosure, refers to an organic group that contains 1, 2, 3, 4, 5, 6, 7, 8, 9, 10, 11, 12, 13, 14, 15, 16, 17, 18, 19, 20, or 30 carbon atoms, or a range of carbon atoms from any two of the foregoing numbers, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains that contains 2, 3, 4, 5, 6, 7, 8, 9, 10, 11, 12, 13, 14, 15, 16, 17, 18, 19, 20, or 30 carbon atoms, or a range of carbon atoms from any two of the foregoing numbers, unless stated otherwise. While a $C_2$-alkynyl can form a triple bond to a carbon of a parent chain, an alkynyl group of three or more carbons can contain more than one triple bond. Where if there is more than 3 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 4 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term generally represented by the notation "$C_x$-$C_y$" (where x and y are whole integers and y>x) prior to a functional group, e.g., "$C_1$-$C_{12}$ alkyl" refers to a number range of carbon atoms. For the purposes of this disclosure any range specified by "$C_x$-$C_y$" (where x and y are whole integers and y>x) is not exclusive to the expressed range, but is inclusive of all possible ranges that include and fall within the range specified by "$C_x$-$C_y$" (where x and y are whole integers and y>x). For example, the term "$C_1$-$C_4$" provides express support for a range of 1 to 4 carbon atoms, but further provides implicit support for ranges encompassed by 1 to 4 carbon atoms, such as 1 to 2 carbon atoms, 1 to 3 carbon atoms, 2 to 3 carbon atoms, 2 to 4 carbon atoms, and 3 to 4 carbon atoms.

The term "cylcoalkenyl", as used in this disclosure, refers to an alkene that contains at least 4 carbon atoms but no more than 12 carbon atoms connected so that it forms a ring. A "cycloalkenyl" for the purposes of this disclosure encompasses from 1 to 4 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "cylcoalkyl", as used in this disclosure, refers to an alkyl that contains at least 3 carbon atoms but no more than 12 carbon atoms connected so that it forms a ring. A "cycloalkyl" for the purposes of this disclosure encompasses from 1 to 4 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "disorder" as used herein is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

The terms "drug," or "therapeutic agent," as used herein, refers to a compound, or a pharmaceutical composition thereof, which is administered to a subject to treat, prevent, or ameliorate one or more symptoms of a disease or disorder.

The term "heterocycle," as used herein, refers to ring structures that contain at least 1 noncarbon ring atom. A "heterocycle" for the purposes of this disclosure encompass from 1 to 4 heterocycle rings, wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In the case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "non-release controlling excipient" as used herein, refers to an excipient whose primary function do not include modifying the duration or place of release of the active substance from a dosage form as compared with a conventional immediate release dosage form.

The term "optionally substituted" refers to a functional group, typically a hydrocarbon or heterocycle, where one or more hydrogen atoms may be replaced with a substituent. Accordingly, "optionally substituted" refers to a functional group that is substituted, in that one or more hydrogen atoms are replaced with a substituent, or unsubstituted, in that the hydrogen atoms are not replaced with a substituent. For example, an optionally substituted hydrocarbon group refers to an unsubstituted hydrocarbon group or a substituted hydrocarbon group.

The term "pharmaceutically acceptable carrier," "pharmaceutically acceptable excipient," "physiologically acceptable carrier," or "physiologically acceptable excipient" as used herein, refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. Examples of "pharmaceutically acceptable carriers" and "pharmaceutically acceptable excipients" can be found in the following, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004.

The term "release controlling excipient" as used herein, refers to an excipient whose primary function is to modify the duration or place of release of the active substance from a dosage form as compared with a conventional immediate release dosage form.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The terms "treat", "treating" and "treatment", as used herein, refers to ameliorating symptoms associated with a disease or disorder (e.g., multiple sclerosis), including preventing or delaying the onset of the disease or disorder symptoms, and/or lessening the severity or frequency of symptoms of the disease or disorder.

The term "subject" as used herein, refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein. For example, a mammalian subject can refer to a human patient.

The term "substituent" refers to an atom or group of atoms substituted in place of a hydrogen atom. For purposes of this invention, a substituent would include deuterium atoms.

The term "substituted" with respect to hydrocarbons, heterocycles, and the like, refers to structures wherein the parent chain contains one or more substituents.

The term "unsubstituted" with respect to hydrocarbons, heterocycles, and the like, refers to structures wherein the parent chain contains no substituents.

A bond indicated by a straight line and a dashed line indicates a bond that may be a single covalent bond or alternatively a double covalent bond. However, in the case where an R group defines an atom that is connected to another atom by a straight line and a dashed line which would exceed its maximum valence if the bond was a double covalent bond then the bond would only be a single covalent bond. For example, where R can be hydrogen and is connected to another atom by a straight line and a dashed line, then hydrogen would only form a single bond even though such a bond is indicated as being a single or double bond.

The syrbactins are a family of bacterial, macrocyclic, non-ribosomal peptide natural products active against the mammalian proteasome. Their α,β-unsaturated lactam functionality reacts covalently with the catalytic Thr1 residue of proteasome catalytic subunits. Given the clinical success of the proteasome inhibitors bortezomib (BTZ), ixazomib, and carfilzomib against cancers such as multiple myeloma and mantle cell lymphoma, intense investigations into the syrbactins followed their initial discovery. Unlike some other proteasome inhibitors, even some used clinically, the syrbactin syringolin A is quite selective for proteasome β subunits over other protein targets, as demonstrated by affinity-based protein profiling. Several syntheses of the natural syrbactins themselves have been reported, and significant work to prepare analogs has been pursued.

The compounds of disclosure have greater solubilities in aqueous solvents than previous generations of syrbactin analogues. Moreover, it was unexpectedly found that compounds of the disclosure were highly selective and potent inhibitors of the β2 subunit of the immunoproteasome. The results were in direct contrast to other syrbactins, like TIR-199, which are selective inhibitors of the constitutive proteasome. While there are several reports of selective inhibitors of the immunoproteasome trypsin-like subunit, most are not drug-like. The enhancement of the activity of the β5 subunit when the β2 subunit is inhibited by the compounds disclosed herein was unexpected and unusual in the context of simple models of enzyme inhibition. Given the preference for a proteasome catalytic activity that is not found in most cells, it was not very surprising that the compounds disclosed herein have weak biological activity against neuroblastoma cells. The compounds of the disclosure are more drug-like and soluble than syrbactins, like TIR-199, and their selective inhibition of the β2 subunit of the immunoproteasome indicates their use in treating disorders and diseases associated with immunoproteasome activity.

The immunoproteasome is a highly efficient proteolytic machinery derived from the constitutive proteasome and is abundantly expressed in immune cells. The immunoproteasome plays a critical role in the immune system because it degrades intracellular proteins, for example, those of viral origin, into small proteins. They are further digested into short peptides to be presented by major histocompatibility complex (MHC) class I molecules. In addition, the immunoproteasome influences inflammatory disease pathogenesis through its ability to regulate T cell polarization. The immunoproteasome is also expressed in nonimmune cell types during inflammation or neoplastic transformation, supporting a role in the pathogenesis of autoimmune diseases and neoplasms.

The immunoproteasome is a large proteolytic machine derived from the constitutive proteasome and plays a critical role in homeostasis and immunity. The constitutive proteasome is expressed ubiquitously in the body, where it degrades ubiquitinated proteins including transcriptional factors and proteins required for cell cycle progression. Since the primary role of the immunoproteasome is to process antigens for presentation on major histocompatibility complex (MHC) class I molecules to CD8+ T lymphocytes, the immunoproteasome degrades various proteins, including viral proteins. Therefore, the immunoproteasome plays an important role during viral infection. The expression of the immunoproteasome is induced by interferon-γ (IFN-γ) and tumor necrosis factor-α (TNF-α) under inflammatory conditions, such as infections, and autoimmune diseases when inflammatory cytokines are present. Accordingly, the immunoproteasome is controlled by factors that impact the immune system. Interestingly, various roles for the immunoproteasome in nonimmune cells have been reported recently, suggesting that there could still be unknown roles for the immunoproteasome.

The immunoproteasome is a subtype of the standard proteasome and differs from the latter by comprising different catalytic subunits and thus function (e.g., see FIG. 1). While, standard proteasome catalytic subunits include β1, β2, and β5, which are constitutively expressed in all cells, the immunoproteasome catalytic subunits, LMP2, MECL-1, and LMP7, are inducible. The basic structure of all proteasome subtypes is essentially the same. Each 20S core particle is composed of four stacked rings of seven subunits each. The two outer rings contain the constitutively expressed α-subunits, which interact with regulatory complexes such as PA28 and PA700. The two inner rings contain the β-subunits. Three of the β-subunits in each ring perform distinct proteolytic activities. In the standard proteasome, activity of the catalytic sub-units β1, β2, and β5 have been classified as caspase-like, trypsin-like, and chymotrypsin-like for cleavage after acidic, basic, and hydrophobic amino acids, respectively (see Table 1).

TABLE 1

Nomenclature and Activity for Proteasome Catalytic Subunits

| Proteasome subunit | Common name | Alternative names | Gene | Activity |
|---|---|---|---|---|
| Beta type-6 | β1 | Y, Delta, LMP19, Pre3 | PSMB6 | Caspase-like |
| Beta type-9 | β1i | Lmp2, RING12, MC7 | PSMB9 | Chymotrypsin-like |
| Beta type-7 | β2 | Z, MC14, Lmp9, Pup1 | PSMB7 | Trypsin-like |
| Beta type-10 | β2i | MECL-1, Lmp10 | PSMB10 | Trypsin-like |
| Beta type-5 | β5 | X, epsilon, Lmp17, MB1, Pre2, Doa3, Prg1 | PSMB5 | Chymotrypsin-like |
| Beta type-8 | β5i | Lmp7, RING10, Y2, C13 | PSMB8 | Chymotrypsin-like |
| Beta type-11 | β5t | Thymus-specific β5 | PSMB11 | Chymotrypsin-like |

The standard catalytic subunits β1, β2, and β5 can be replaced in nascent proteasome cores by the inducible subunits LMP2, MECL-1, and LMP7, respectively. While the MECL-1 and LMP7 subunits perform the same type of activities as the β2 and β5, the LMP2 subunit performs chymotrypsin-like activity and cleaves after hydrophobic amino acids. It has been suggested that the altered activity of the LMP2 subunit facilitates the generation of peptides for antigen presentation, which requires peptides with hydrophobic amino acids in the C-terminal position. Each catalytic subunit is expressed with a propeptide that ranges in size from 20 to 72 amino acids. Cleavage of the propeptide is essential for maturation of the 20S core and activation of the catalytic threonine residue. Thus, the difference in the molecular mass of the unprocessed and the mature protein allows one to distinguish these two species on a high-percentage sodium dodecyl sulfate gel.

Standard proteasomes are constitutively expressed in nearly all mammalian cells. In contrast, immunoproteasome expression is generally lower under basal conditions, but can be significantly upregulated when cells are exposed to various factors, such as IFN-γ, or environmental stressors, such as oxidative stress. An exception to this generalization is the cells of the immune system, which can constitutively express immunoproteasome at high levels. For example, cells in the spleen contain nearly all of immunoproteasomes subunits and only low levels of the standard proteasome subunits.

Induction of immunoproteasome subunit expression by IFN-γ has been well established for both cultured immune cells and cultured nonimmune cells, such as neurons and epithelial cells of the retina. This cytokine-induced expression results from binding of the Stat-1 and IRF-1 transcription factors to multiple IFN-γ consensus/activation sequences in the promoter region of the LMP2, LMP7, and MECL-1 genes. Other cytokines, such as IFNα/β, lipopolysaccharide, and TNFα also elicit an inflammatory response that involves increased immunoproteasome expression.

Based on the proteolysis of model peptide substrates, the active sites have been classified as caspase-like, trypsin-like, and chymotrypsin-like for cleavage after acidic, basic, and hydrophobic amino acids, respectively. For the immunoproteasome, some differences in catalytic activity and peptide generation have been noted. Comparing activity of the β2 and β5 standard subunits with the corresponding immunoproteasome subunits MECL-1 and LMP7, the specificity is generally the same. However, comparison of cleavage after branched chain and hydrophobic residues for standard and immunoproteasome has not been consistent; both increased and decreased activity have been reported for the immunoproteasome. The discrepancy in data is due in part to heterogeneity of proteasome subtypes and cell-specific endogenous regulators in the tissue analyzed, and the inability of model peptide substrates to distinguish between proteasome subtypes. Cleavage after acidic residues, which is accomplished by the β1 standard subunit, is nearly abolished in the immunoproteasome. Instead, there is a shift to chymotrypsin-like activity for LMP2, which promotes the generation of MHC class I-compatible peptides containing hydrophobic C-terminal anchors.

While the mechanism of hydrolysis (involving the active-site Thr1, Asp17, and Lys33) is the same for each subunit, the specificity of cleavage for each active site is determined by the amino acids that make up the Si binding pocket (residues 20, 31, 35, 45, 49, 53, 115, 116), which is where protein substrates bind prior to cleavage. Alignment of sequences comparing the standard with their immunoproteasome subunit correlate generally shows high conservation of the amino acids that make up the binding pocket, except for LMP2 and β5t. LMP2 contains two prominent substitutions compared with residues in β1; the β1 Thr21 is replaced by Val and the Arg45 is replaced by Leu. These substitutions minimize the size of the Si pocket of LMP2 and change the overall charge of the local environment from positive to neutral. These changes in primary sequence and charge state of the LMP2 binding pocket could explain the drastic reduction in the caspase-like activity of the immunoproteasome. One other noteworthy change occurs in positions 115 and 116 in β5 and LMP7; substitution of Ser115 for a Glu and substitution of Glu116 for His in β5 and LMP7, respectively, would alter the size and polarity of the binding pocket. These structural changes could alter the substrate preference of each subunit and, consequently, result in the production of different peptides.

Figure 5A:
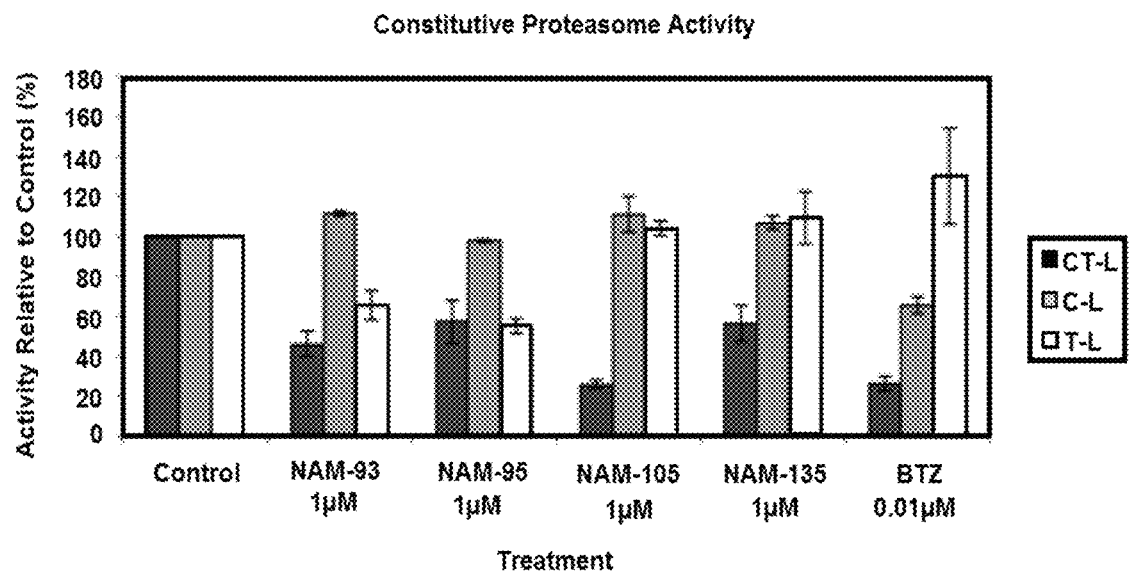
FIG. 5A-B provides charts showing the effect of the compounds of the disclosure on in vitro proteasome activity. (A) Constitutive and (B) immunoproteasome were treated with 1.0 µM 1 (NAM-105), 2 (NAM-135), 5 (NAM-93) and 6 (NAM-95) for 2 hours. Bortezomib (BTZ) was included as a control. The sub-catalytic activities were then measured using luminogenic substrates as described herein. Data shown are representative of three independent experiments (n=3).
Figure 5B:
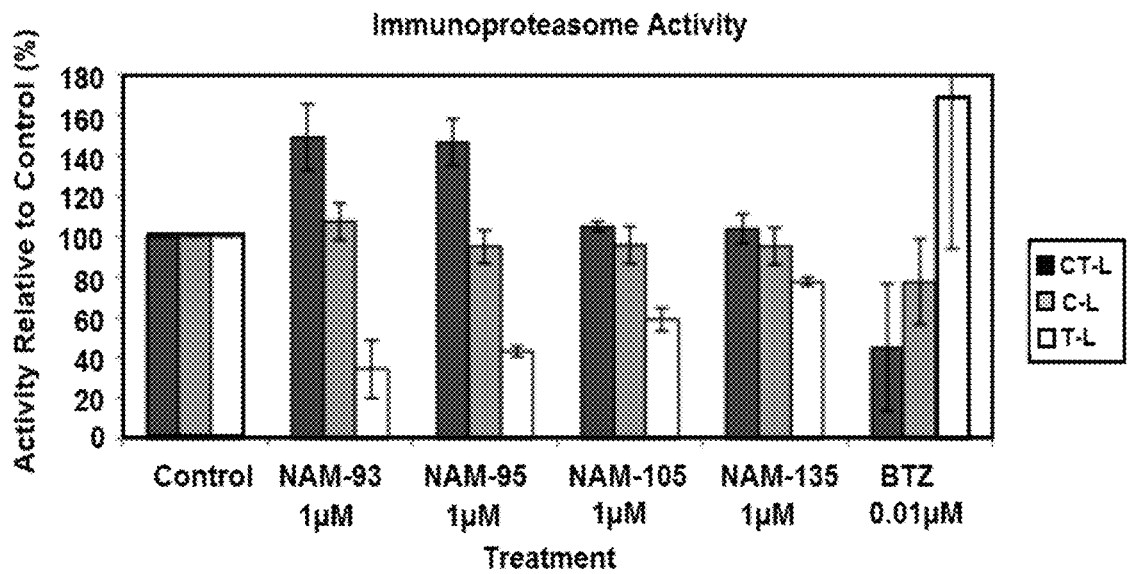

The disclosure provides for new and innovative compounds that have been shown to preferentially inhibit the immunoproteasome. In screening assays presented herein (see FIG. 5), compounds of the disclosure were tested against three different proteasome activities, caspase-like (beta1), trypsin-like (beta2), and chymotrypsin like (beta5). The assays were run against constitutive proteasome and immunoproteasome. The screens were performed with compounds at concentration of 1 μM. The approved drug bortezomib was included in the assays for comparison, but used at much lower concentrations because of its potency. One compound (NAM-105) showed a pattern of activity similar to TIR-199, with the greatest activity vs. the chymotrypsin-like activity of the constitutive proteasome. While the activity of two compounds (NAM-93 and NAM-95) vs. the immunoproteasome yielded surprising and unexpected results. First, there is the good inhibition vs. the trypsin-like activity. This selectivity has been difficult to obtain in any class of proteasome inhibitors. It is also interesting that both of these compounds seem to stimulate the chymotrypsin-like activity of the immunoproteasome only. Accordingly, the compounds of the disclosure comprise a new class of immunoproteasome inhibitors that can provide additional and possibly new treatment options for subjects suffering from various diseases and disorders, especially those subjects suffering from an inflammatory disorder, an autoimmune disease or a neurodegenerative disorder.

In a particular embodiment, the disclosure provides for a compound comprising a structure of Formula I:

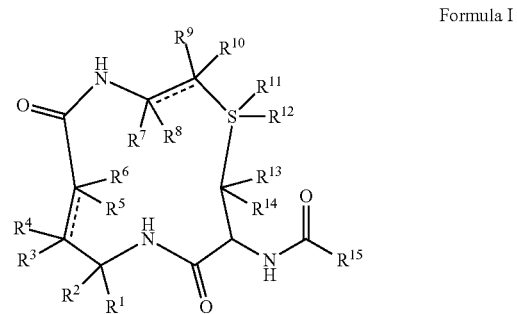

Formula I or a pharmaceutically acceptable salt, or solvate thereof, wherein, $R^1$ and $R^2$ are independently selected from the group consisting of H, cyano, an optionally substituted ($C_1$-$C_6$) alkyl and an optionally substituted cycloalkyl;

$R^3$-$R^{10}$, $R^{13}$ and $R^{14}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanate, isocyanato, an optionally substituted ($C_1$-$C_6$)alkyl, an optionally substituted ($C_1$-$C_6$)alkenyl, an optionally substituted ($C_1$-$C_6$)alkynyl, an optionally substituted ($C_1$-$C_6$)hetero-alkyl, an optionally substituted ($C_1$-$C_6$)hetero-alkenyl, an optionally substituted ($C_1$-$C_6$)hetero-alkynyl, an optionally substituted ($C_3$-$C_8$)cycloalkyl, an optionally substituted aryl, and an optionally substituted heterocycle;

$R^{11}$ and $R^{12}$ are independently selected from H, =O, and an optionally substituted ($C_1$-$C_6$)alkyl, wherein $R^{11}$ and/or $R^{12}$ may also be absent;

$R^{15}$ is selected from the group consisting of

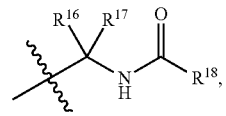

an optionally substituted heterocycle, an optionally substituted aryl, an optionally substituted benzyl, and an optionally substituted ($C_3$-$C_8$)cycloalkyl, —$CH_2(R^{19})$, —$CH(R^{19})_2$, —$NH(R^{19})$ and —$N(R^{19})_2$;

$R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanate, isocyanato, an optionally substituted ($C_1$-$C_6$)alkyl, an optionally substituted ($C_2$-$C_6$)alkenyl, an optionally substituted ($C_2$-$C_6$)alkynyl, an optionally substituted ($C_1$-$C_6$)hetero-alkyl, an optionally substituted ($C_2$-$C_6$)hetero-alkenyl, an optionally substituted ($C_2$-$C_6$)hetero-alkynyl, an optionally substituted ($C_3$-$C_8$)cycloalkyl, an optionally substituted aryl, and an optionally substituted heterocycle;

$R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted (C$_3$-C$_8$)cycloalkyl; and R$^{19}$ is selected from the group consisting of an optionally substituted (C$_3$-C$_{16}$) alkyl, an optionally substituted (C$_3$-C$_{16}$)alkenyl, an optionally substituted (C$_3$-C$_{16}$)alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

In a certain embodiment, the disclosure provides for a compound that comprises the structure of Formula II:

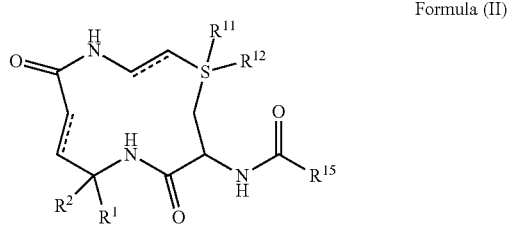

Formula (II)

or a pharmaceutically acceptable salt, or solvate thereof, wherein,

R$^1$ and R$^2$ are independently selected from the group consisting of H, cyano, an optionally substituted (C$_1$-C$_6$) alkyl and an optionally substituted cycloalkyl;

R$^{11}$ and R$^{12}$ are independently selected from H, =O, and an optionally substituted (C$_1$-C$_6$)alkyl, wherein R$^{11}$ and/or R$^{12}$ may also be absent;

R$^{15}$ is selected from the group consisting of

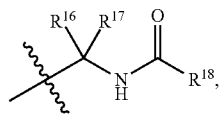

an optionally substituted heterocycle, an optionally substituted aryl, an optionally substituted benzyl, and an optionally substituted (C$_3$-C$_8$)cycloalkyl, —CH$_2$(R$^{19}$), —CH(R$^{19}$)$_2$, —NH(R$^{19}$) and —N(R$^{19}$)$_2$;

R$^{16}$ and R$^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted (C$_1$-C$_6$)alkyl, an optionally substituted (C$_2$-C$_6$)alkenyl, an optionally substituted (C$_2$-C$_6$)alkynyl, an optionally substituted (C$_1$-C$_6$)hetero-alkyl, an optionally substituted (C$_2$-C$_6$)hetero-alkenyl, an optionally substituted (C$_2$-C$_6$)hetero-alkynyl, an optionally substituted (C$_3$-C$_8$)cycloalkyl, an optionally substituted aryl, and an optionally substituted heterocycle;

R$^{18}$ is selected from the group consisting of —CH$_2$(R$^{19}$), —CH(R$^{19}$)$_2$, —NH(R$^{19}$), —N(R$^{19}$)$_2$, an optionally substituted heterocycle, an optionally substituted aryl, an optionally substituted benzyl, and an optionally substituted (C$_3$-C$_8$)cycloalkyl; and R$^{19}$ is selected from the group consisting of an optionally substituted (C$_3$-C$_{16}$) alkyl, an optionally substituted (C$_3$-C$_{16}$)alkenyl, an optionally substituted (C$_3$-C$_{16}$)alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

In a further embodiment, the disclosure provides for a compound that comprises the structure of Formula II(a):

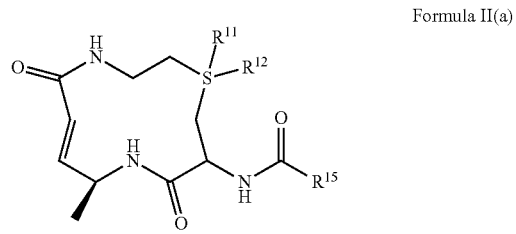

Formula II(a)

or a pharmaceutically acceptable salt, or solvate thereof, wherein,

R$^{11}$ and R$^{12}$ are independently selected from H, =O, and an optional substituted (C$_1$-C$_6$)alkyl, or wherein R$^{11}$ and/or R$^{12}$ may also be absent;

R$^{15}$ is selected from the group consisting of

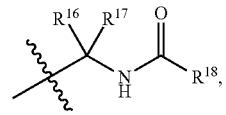

an optionally substituted heterocycle, an optionally substituted aryl, an optionally substituted benzyl, and an optionally substituted (C$_3$-C$_8$)cycloalkyl, —CH$_2$(R$^{19}$), —CH(R$^{19}$)$_2$, —NH(R$^{19}$) and —N(R$^{19}$)$_2$;

R$^{16}$ and R$^{17}$ are independently selected from the group consisting of H, cyano, carboxamide, carboxyl, nitro, ester, an optionally substituted (C$_1$-C$_6$)alkyl, an optionally substituted (C$_2$-C$_6$)alkenyl, an optionally substituted (C$_2$-C$_6$)alkynyl, an optionally substituted (C$_1$-C$_6$)hetero-alkyl, an optionally substituted (C$_2$-C$_6$)hetero-alkenyl, an optionally substituted (C$_2$-C$_6$)hetero-alkynyl, an optionally substituted (C$_3$-C$_8$)cycloalkyl, an optionally substituted aryl, and an optionally substituted heterocycle;

R$^{18}$ is selected from the group consisting of —CH$_2$(R$^{19}$), —CH(R$^{19}$)$_2$, —NH(R$^{19}$), —N(R$^{19}$)$_2$, an optionally substituted heterocycle, an optionally substituted aryl, an optionally substituted benzyl, and an optionally substituted (C$_3$-C$_8$)cycloalkyl; and R$^{19}$ is selected from the group consisting an optionally substituted (C$_3$-C$_{16}$) alkyl, an optionally substituted (C$_3$-C$_{16}$)alkenyl, an optionally substituted (C$_3$-C$_{16}$)alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

In a yet a further embodiment, the disclosure provides for a compound that comprises the structure of Formula II(b):

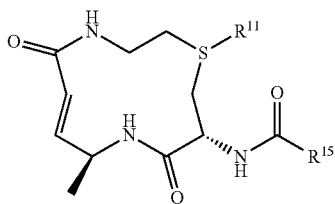

Formula II(b)

or a pharmaceutically acceptable salt, or solvate thereof, wherein, $R^{11}$ is =O or is absent;

$R^{15}$ is selected from the group consisting of

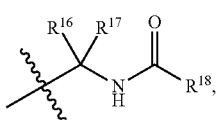

an optionally substituted heterocycle, an optionally substituted aryl, an optionally substituted benzyl, and an optionally substituted $(C_3-C_8)$cycloalkyl, —$CH_2(R^{19})$, —$CH(R^{19})_2$, —$NH(R^{19})$ and —$N(R^{19})_2$;

$R^{16}$ and $R^{17}$ are independently selected from the group consisting of H, cyano, carboxamide, carboxyl, nitro, ester, an optionally substituted $(C_1-C_6)$alkyl, an optionally substituted $(C_2-C_6)$alkenyl, an optionally substituted $(C_2-C_6)$alkynyl, an optionally substituted $(C_1-C_6)$hetero-alkyl, an optionally substituted $(C_2-C_6)$hetero-alkenyl, an optionally substituted $(C_2-C_6)$hetero-alkynyl, an optionally substituted $(C_3-C_8)$cycloalkyl, an optionally substituted aryl, and an optionally substituted heterocycle;

$R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted $(C_3-C_8)$cycloalkyl; and $R^{19}$ is selected from the group consisting of an optionally substituted $(C_3-C_{16})$ alkyl, an optionally substituted $(C_3-C_{16})$alkenyl, an optionally substituted $(C_3-C_{16})$alkynyl, an optionally substituted $(C_3-C_{15})$hetero-alkyl, an optionally substituted $(C_3-C_{15})$hetero-alkenyl, an optionally substituted $(C_3-C_{15})$hetero-alkynyl, an optionally substituted heterocycle, an optionally substituted aryl, an optionally substituted benzyl, and an optionally substituted $(C_3-C_8)$cycloalkyl.

In a certain embodiment, $R^{15}$ is selected from the group consisting of:

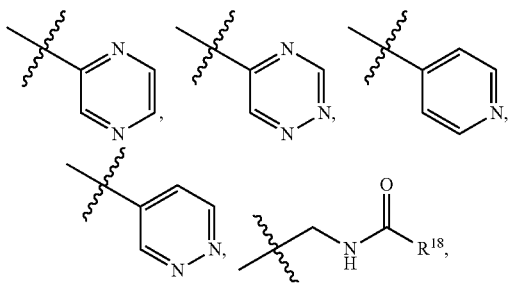

-continued

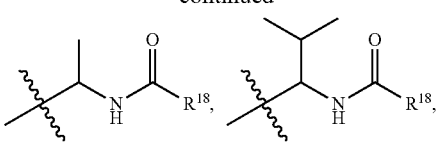

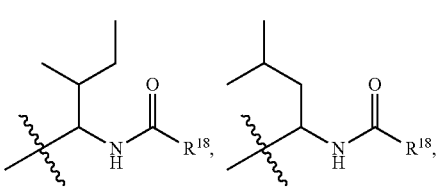

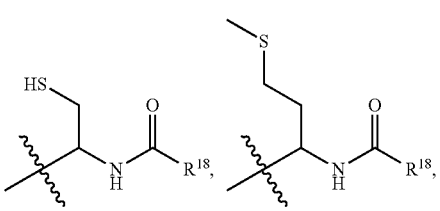

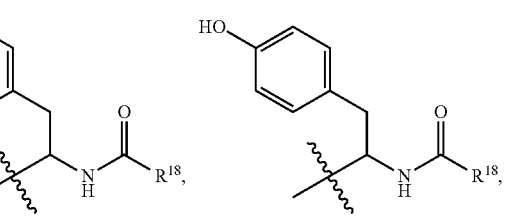

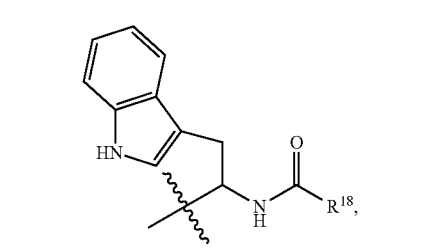

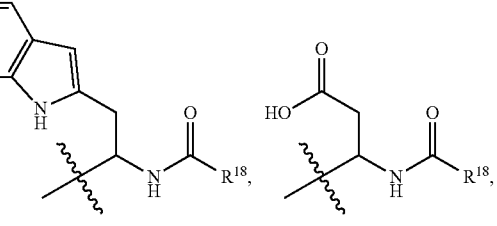

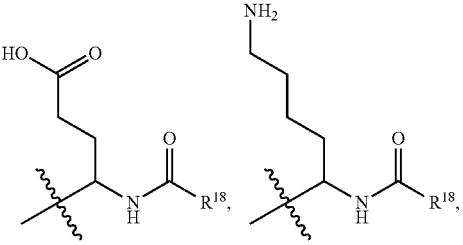

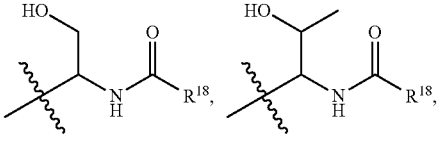

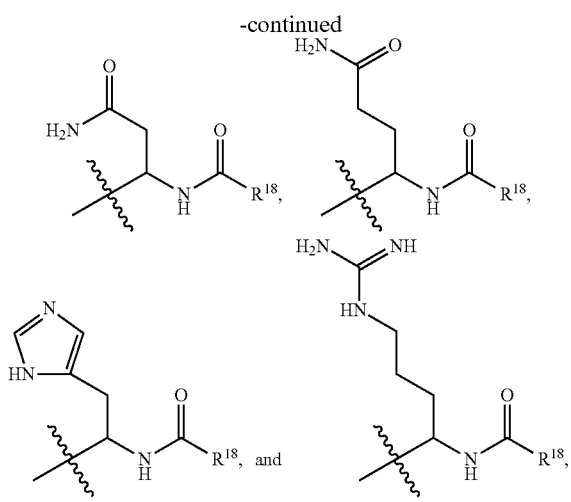

wherein,

R$^{18}$ is selected from the group consisting of —CH$_2$(R$^{19}$), —CH(R$^{19}$)$_2$, —NH(R$^{19}$), —N(R$^{19}$)$_2$, an optionally substituted heterocycle, an optionally substituted aryl, an optionally substituted benzyl, and an optionally substituted (C$_3$-C$_8$)cycloalkyl; and R$^{19}$ is selected from the group consisting an optionally substituted (C$_3$-C$_{16}$) alkyl, an optionally substituted (C$_3$-C$_{16}$)alkenyl, an optionally substituted (C$_3$-C$_{16}$)alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

In a yet another embodiment, the disclosure provides for a compound that comprises the structure of Formula III:

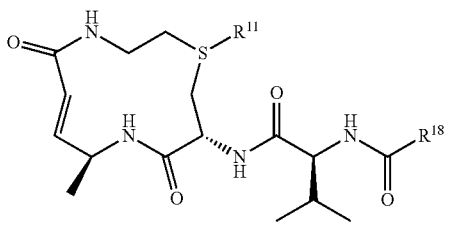

Formula III or a pharmaceutically acceptable salt, or solvate thereof, wherein,

R$^{11}$ is =O or is absent;

R$^{18}$ is selected from the group consisting of —CH$_2$(R$^{19}$), —CH(R$^{19}$)$_2$, —NH(R$^{19}$), —N(R$^{19}$)$_2$, an optionally substituted heterocycle, an optionally substituted aryl, an optionally substituted benzyl, and an optionally substituted (C$_3$-C$_8$)cycloalkyl; and R$^{19}$ is selected from the group consisting an optionally substituted (C$_3$-C$_{16}$) alkyl, an optionally substituted (C$_3$-C$_{16}$)alkenyl, an optionally substituted (C$_3$-C$_{16}$)alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

In a further embodiment, R$^{18}$ is selected from octanyl, nonanyl, decanyl, undecanyl, dodecanyl, tridecanyl, tetradecanyl, pentadecanyl, hexadecanyl, benzene, phenol, toluene, ethyl benzene, p-xylene, m-xylene, mesitylene, durene, 2-phyenylhexane, biphenyl, aniline, nitrobenzene, benzoic acid, naphthalene, anthracene, phenanthrene, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, quinolizidine and 1-ethyl-4-isobutylbenzene.

In yet a further embodiment, R$^{19}$ is selected from octanyl, nonanyl, decanyl, undecanyl, dodecanyl, tridecanyl, tetradecanyl, pentadecanyl, hexadecanyl, benzene, phenol, toluene, ethyl benzene, p-xylene, m-xylene, mesitylene, durene, 2-phyenylhexane, biphenyl, aniline, nitrobenzene, benzoic acid, naphthalene, anthracene, phenanthrene, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, quinolizidine and 1-ethyl-4-isobutylbenzene.

In a certain embodiment, the disclosure provides for a compound comprising the structure of:

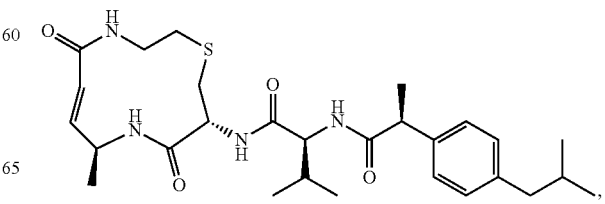

-continued

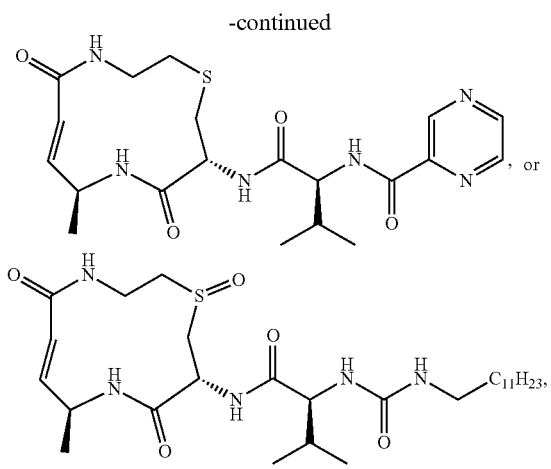

or a pharmaceutically acceptable salt, or solvate thereof.

The compounds disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

Disclosed herein are pharmaceutical compositions comprising one or more compounds disclosed herein, or a pharmaceutically acceptable salt, solvate, or prodrug thereof, as an active ingredient, combined with a pharmaceutically acceptable vehicle, carrier, diluent, or excipient, or a mixture thereof; in combination with one or more pharmaceutically acceptable excipients or carriers When the compound disclosed herein contains an acidic or basic moiety, it may also be disclosed as a pharmaceutically acceptable salt. Examples of pharmaceutically acceptable salts can be found in Berge et al., *J. Pharm. Sci.* 66:1-19 (1977); and "Handbook of Pharmaceutical Salts, Properties, and Use," Stah and Wermuth, Ed., Wiley-VCH and VHCA, Zurich, 2002, which are incorporated herein.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, include, but are not limited to: inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound as disclosed herein may also be designed as a prodrug, which is a functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. The following references which are incorporated herein, provide methods to design and make prodrugs of the disclosure: Harper, *Progress in Drug Research* 4:221-294 (1962); Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 5:265-287 (1999); Pauletti et al., *Adv. Drug. Delivery Rev.* 27:235-256 (1997); Mizen et al., *Pharm. Biotech.* 11:345-365 (1998); Gaignault et al., *Pract. Med. Chem.* 671-696 (1996); Asgharnejad in "Transport Processes in Pharmaceutical Systems," Amidon et al., Ed., Marcell Dekker, 185-218, 2000; Balant et al., *Eur. J. Drug Metab. Pharmacokinet.* 15: 143-53 (1990); Balimane and Sinko, *Adv. Drug Delivery Rev.* 39: 183-209 (1999); Browne, *Clin. Neuropharmacol.* 201-12 (1997); Bundgaard, *Arch. Pharm. Chem.* 86:1-39 (1979); Bundgaard, *Controlled Drug Delivery* 17:179-96 (1987); Bundgaard, *Adv. Drug Delivery Rev.* 8:1-38 (1992); Fleisher et al., Adv. Drug Delivery Rev. 19:115-130 (1996); Fleisher et al., *Methods Enzymol.* 112: 360-381 (1985); Farquhar et al., *J. Pharm. Sci.* 72:324-325 (1983); Freeman et al., *J. Chem. Soc., Chem. Commun.* 875-877 (1991); Friis and Bundgaard, *Eur. J. Pharm. Sci.* 4:49-59 (1996); Gangwar et al., Des. Biopharm. Prop. Prodrugs Analogs, 409-421 (1977); Nathwani and Wood, *Drugs* 45:866-94 (1993); Sinhababu and Thakker, *Adv. Drug Delivery Rev.* 19:241-273 (1996); Stella et al., *Drugs* 29:455-73 (1985); Tan et al., *Adv. Drug Delivery Rev.* 39:117-151 (1999); Taylor, *Adv. Drug Delivery Rev.* 19:131-148 (1996); Valentino and Borchardt, *Drug Discovery Today*

2:148-155 (1997); Wiebe and Knaus, *Adv. Drug Delivery Rev.* 39:63-80 (1999); Waller et al., *Br. J. Clin. Pharmac.* 28:497-507 (1989).

The compounds disclosed herein can generally be made from commercially available starting materials, such as thialysine (S-aminoethyl-L-cysteine). Accordingly, many different compounds can be generated and at quantities sufficient for running various biological and chemical tests. The compounds disclosed herein were found to have greater solubility than other proteasome inhibitors, like TIR-199.

Disclosed herein are pharmaceutical compositions in modified release dosage forms, which comprise a compound as disclosed herein, or a pharmaceutically acceptable salt, solvate, or prodrug thereof, and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions disclosed herein may also comprise non-release controlling excipients or carriers.

As described herein, the pharmaceutical compositions of the disclosure additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and techniques for the preparation thereof, which is incorporated herein in its entirety. Except insofar as any conventional carrier medium is incompatible with the compounds of the disclosure, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil, safflower oil, sesame oil, olive oil, corn oil and soybean oil; glycols, such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

The disclosure provides in a particular embodiment, pharmaceutical compositions in enteric coated dosage forms, which comprise a compound as disclosed herein, or a pharmaceutically acceptable salt, solvate, or prodrug thereof, and one or more release controlling excipients or carriers for use in an enteric coated dosage form. In a further embodiment, the pharmaceutical compositions may also comprise non-release controlling excipients or carriers.

The disclosure further provides in a certain embodiment, pharmaceutical compositions in effervescent dosage forms, which comprise a compound as disclosed herein, or a pharmaceutically acceptable salt, solvate, or prodrug thereof, and one or more release controlling excipients or carriers for use in an effervescent dosage form. In another embodiment, the pharmaceutical compositions may also comprise non-release controlling excipients or carriers.

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-.beta.-cyclodextrin, and sulfobutylether 7-β-cyclodextrin (CAPTISOLR®, CyDex, Lenexa, Kans.).

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are formulated as ready-to-use sterile solutions. In another embodiment, the pharmaceutical compositions are formulated as sterile dry soluble products, including lyophilized powders and hypodermic tablets, to be reconstituted with a vehicle prior to use. In yet another embodiment, the pharmaceutical compositions are formulated as ready-to-use sterile suspensions. In yet another embodiment, the pharmaceutical compositions are formulated as sterile dry insoluble products to be reconstituted with a vehicle prior to use. In still another embodiment, the pharmaceutical compositions are formulated as ready-to-use sterile emulsions.

The pharmaceutical compositions disclosed herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Additionally, disclosed herein are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound as disclosed herein, or a pharmaceutically acceptable salt, solvate, or prodrug thereof, and one or more release controlling and non-release controlling excipients or carriers, such as those excipients or carriers suitable for a disruptable semi-permeable membrane and as swellable substances.

The disclosure also provides herein, pharmaceutical compositions in a dosage form for oral administration to a subject, which comprise a compound as disclosed herein, or a pharmaceutically acceptable salt, solvate, or prodrug thereof, and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In a particular embodiment, the disclosure provides for pharmaceutical compositions that comprise about 0.1 to about 1000 mg/mL, about 1 to about 500 mg/mL, about 2 to about 100 mg/mL, about 10 mg/mL to 1 mg/mL, about 5 mg/mL to 1 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 10 mg/mL, about 15 mg/mL, about 20 mg/mL, about 30 mg/mL, about 40 mg/mL, about 50 mg/mL, about 100 mg/mL, about 500 mg/mL of one or more compounds as disclosed herein, for administering intravenously or subcutaneously. The pharmaceutical compositions may further comprise inactive ingredients such as mannitol, sodium chloride, and sorbitol.

In another embodiment, the disclosure provides for pharmaceutical compositions that comprise about 0.1 to about 1000 mg, about 1 to about 500 mg, about 2 to about 100 mg, about 1 mg, about 2 mg, about 3 mg, about 5 mg, about 10 mg, about 15 mg, about 20 mg, about 30 mg, about 40 mg, about 50 mg, about 100 mg, about 500 mg of one or more compounds as disclosed herein, in the form of pills or tablets for oral administration. In yet another embodiment, the pharmaceutical compositions may further comprise inactive ingredients such as ethylcellulose, dibutyl sebacate, polyvinyl pyrroliodone, sodium stearyl fumarate, colloidal silicon dioxide, and polyvinyl alcohol.

The pharmaceutical compositions disclosed herein may be disclosed in "unit-dosage forms" or "multiple-dosage forms." "Unit-dosage forms," as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampouls, syringes, and individually packaged tablets and capsules. Unit-dosage forms may be administered in fractions or multiples thereof. A "multiple-dosage form" as used herein, refers to a plurality of identical unit-dosage forms packaged in a single container to be administered in segregated unit-dosage form. Examples of multiple-dosage forms include vials, bottles of tablets or capsules, or bottles of pints or gallons.

The compound as disclosed herein may be administered alone, or in combination with one or more other compounds disclosed herein, and one or more other active ingredients. The disclosure further provides that a pharmaceutical composition disclosed herein may be formulated for various dosage forms for a particular mode of administration, including oral, parenteral, and topical administration. The pharmaceutical compositions of the disclosure may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see e.g., Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case where the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case where the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

Administration of the pharmaceutical compositions disclosed herein may begin after the subject is determined to have a disorder or suspected of having a disorder which is treatable by a compound disclosed herein. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters)) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or di-calcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release a compound of the disclosure only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The compounds disclosed herein can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compound of the disclosure may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of the disclosure include ointments, pastes, creams, lotions, gels, powders, solutions, sprays, aerosols, inhalants or patches. A compound disclosed herein is admixed under sterile conditions with a pharmaceutically acceptable carrier and any preservatives or buffers, as may be required. Ophthalmic formulation, ear drops, and eye drops are also contemplated as being within the scope of this disclosure. Additionally, the disclosure contemplates the use of transdermal patches, which have the added advantage of providing controlled delivery of a compound disclosed herein to the body. Such dosage forms are made by dissolving or dispensing a compound of the disclosure in a proper medium. Absorption enhancers can also be used to increase the flux of the compound across the skin. The rate can be controlled by either providing a rate controlling membrane or by dispersing the compound in a polymer matrix or gel.

Depending on the disorder to be treated and the subject's condition, one or more compounds disclosed herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligrams, from about 0.1 to about 500 milligrams, or from 0.5 about to about 100 milligrams active ingredient(s) per dosage unit, and if the condition of the patient requires, the dose can, by way of alternative, be administered as a continuous infusion.

In a certain embodiment, an appropriate dosage level for a compound disclosed herein is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

In a particular embodiment, the compounds disclosed herein can be used to inhibit the activity of an immunoproteasome. In a certain embodiment, the compounds disclosed herein can be used as a therapeutic agent to treat disorders that are associated with a dysregulated immunoproteasome or disorders that are treatable by inhibiting immunoproteasome activity. The list of human diseases that have been linked to deregulation of the immunoproteasome has grown exponentially over the past decade. However, the data supporting this link are often indirect. For example, increased immunoproteasome expression, altered immunoproteasome activity, and/or accumulation of ubiquitinated protein in the diseased tissue have been reported in multiple diseases, including several neurodegenerative diseases of the brain and retina. These diseases share oxidation and/or inflammation as part of the disease mechanism and, thus, changes in immunoproteasome expression and activity are likely a consequence of the altered cellular condition rather than part of the primary disease mechanism. Experiments in cultured cells support this idea. Exposure of cells to sublethal levels of oxidative stress, inflammatory cytokines, or cellular expression of aggregate-prone proteins, which is an integral part of the mechanism of Huntington disease, all induce expression of iummoproteasome. While the increased expression of the immunoproteasome in diseased tissue provides limited mechanistic information, it has opened the door to novel therapeutic options that use inhibitors (i.e., PR-957, PR-924, IPSI-001) that selectively target the iummoproteasome catalytic subunits. This approach is designed to either specifically kill cells expressing high levels of immunoproteasome, as is the goal with cancer, or inhibit signaling pathways, such as the proinflammatory NF-κB pathway in autoimmune disease. Since immunoproteasome inhibitors should not affect the activity of the standard proteasome, which is constitutively present in all cells, immunoproteasome inhibitors should be less toxic and have reduced off-target side effects compared with other broad-spectrum proteasome inhibitors, such as bortezomib and carfilozomib.

The immunoproteasome is involved in the pathogenesis of numerous diseases and disorders, by influencing T cell polarization, signaling through the nuclear factor-κB (NF-κB) pathway, and the production of inflammatory cytokines by macrophages. Immunoproteasome inhibitors, like ONX-0914, have shown effectiveness in animals models for treating or ameliorating symptoms associated with various diseases and disorders, including but not limited to, inflammatory diseases, like colitis (Basler et al., *Journal of Immunology*, 185(1):634-641 (2010)), asthma (Volkov et al., *PLoS ONE*, 8(4):e60565 (2013)), inflammatory bowel disease (Basler et al., *Journal of Immunology*, 185(1):634-641 (2010)), Alzheimer's disease (One et al., *Brain* 136(5):1415-1431 (2013)), and Nakajo-Nishimura syndrome (Arimochi et al., Inflammation and Regeneration, 36:13 (2016)); autoimmune diseases, like autoimmune encephalomyelitis (Basler et al., *EMBO Molecular Medicine* 6(2):226-238 (2014)), thyroiditis (Nagayama et al., *Clinical & Experimental Immunology* 168(3):268-273 (2012)) rheumatoid arthritis (see Muchamuel et al., *Nature Medicine* 15(7):781-787 (2009)), multiple sclerosis (Basler et al., *EMBO Molecular Medicine* 6(2):226-238 (2014)), systemic lupus erythematosus (Ichikawa et al., *Arthritis Rheum* 64:493-503 (2012)) and Sjögren's syndrome (Krause et al., *Rheumatic Diseases* 65(8):1021-1027 (2006)); obesity (Kimura et al., *Scientific Reports* 15883 (2015)); metabolic disorders, such as dyslipidemia (Kimura et al., *Scientific Reports* 15883 (2015)), and hyperglycemia (Kimura et al., *Scientific Reports* 15883 (2015)); and hematological malignancies, like multiple myeloma (Singh et al., *Br J Haematol,* 152 (2):155-63 (2011)), and mantle cell lymphoma (Zhang et al., *Mol Cancer Ther* 12(11):2494-504 (2013)). Preclinical studies with immunoproteasome inhibitors for the treatment of rheumatoid arthritis, inflammatory bowel disease, and cancer have also shown promise.

Thus, molecules that selectively inhibit immunoproteasome activities could have therapeutic uses different from approved proteasome inhibitor drugs, which are essentially only anticancer agents against multiple myeloma and mantle cell lymphoma. That is, the compounds disclosed herein can be used to treat cancer, but also used to treat diseases unrelated to cancer wherein aberrant regulation of the immunoproteasome has been observed. Such diseases include Huntington disease, Alzheimer's disease, macular degeneration, inflammatory bowel disease (Crohn disease, ulcerative colitis), and rheumatoid arthritis (Sjögren's syndrome). In some cases, immunoproteasome specific inhibitors that directly target the catalytic core might be useful. In other instances, inhibitors that alter the activity of immunoproteasome-specific subunits might lead to novel treatment options. For example, the immunoproteasome-specific subunits LMP2 or LMP7 are increased in Huntington disease neurodegeneration and tissue-specific upregulation of LMP7 is characteristic in patients with Sjogren's syndrome.

In a particular embodiment, the compounds disclosed herein can be used to treat a cancer in a subject, wherein the cancer can be treated by inhibiting immunoproteasome activity. Examples of such cancers, include, but are not limited to, colorectal cancer, malignant pleural mesothelioma (MPM), breast cancer, glioblastoma multiforme (GBM), Lung cancer, cervical cancer, gastric cancer, leukemia, multiple myeloma, and non-Hodgkin's lymphoma. In an alternate embodiment, the compounds disclosed herein can be used to treat a neurodegenerative disorder in a subject, wherein the neurodegenerative disorder can be treated by inhibiting immunoproteasome activity. Examples of such neurodegenerative disorders include, but are not limited to, Huntingdon's disease, Alzheimer's disease, Parkinson's disease, Amyotrophic lateral sclerosis, and dementia.

In a particular embodiment, the compounds disclosed herein can be used as immunomodulators. In a further embodiment, a compound disclosed herein can be used to suppress a subject's immune response. In yet another alternate embodiment, the compounds disclosed herein can be used to treat an autoimmune disease in a subject, wherein the autoimmune disease can be treated by inhibiting immunoproteasome activity. Examples of such autoimmune diseases, include, but are not limited to, macular degeneration, inflammatory bowel disease, Crohn's disease, ulcerative colitis, rheumatoid arthritis, Sjogren's syndrome, systemic lupus erythematosus, celiac sprue disease, pernicious anemia, vitiligo, scleroderma, psoriasis, Hashimoto's disease, Addison's disease, Graves' disease, reactive arthritis and type 1 diabetes.

The compounds or pharmaceutical compositions of the disclosure may be administered at a suitable dosage level and a suitable route of administration to effectively treat the neurodegenerative disorder or autoimmune disorder. Thus, the expression "effective amount" as used herein, refers to a sufficient amount of a compound disclosed herein to inhibit the activity of an immunoproteasome. The exact amount of compound required to be effective will vary from subject to subject, depending on the species, age, and general condition of the subject, the severity of the disorder, the type of disorder, mode of administration, and the like.

The compounds of the disclosure are preferably formulated in dosage unit form for ease of administration and uniformity of dosage. It should be understood, however, that the total daily usage of the compounds and pharmaceutical compositions of the disclosure will be decided largely by the attending physician within the scope of sound medical judgment. The specific therapeutically effective dose level for any particular patient or organism will depend upon a variety of factors, including, but not limited to, the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds disclosed herein may also be combined or used in combination with one or more therapeutic agents, including palliative agents, useful in the treatment, prevention, or amelioration of one or more symptoms of a disorder associated with deregulated immunoproteasome activity and/or NF-kB activity, such as inflammatory disorders, neurodegenerative disorders, or autoimmune disorders, etc. Or, by way of example only, the therapeutic effectiveness of a compound disclosed herein may be enhanced by administration of an adjuvant (i.e., by itself the adjuvant may only have minimal therapeutic benefit, but in combination with another therapeutic agent, the overall therapeutic benefit to the subject is enhanced).

Such other agents, adjuvants, or drugs, may be administered, by a route and in an amount suitable for simultaneous or sequential administration with a compound disclosed herein. When a compound disclosed herein is used contemporaneously with one or more other drugs, a pharmaceutical composition containing such other drugs in addition to the compound disclosed herein may be utilized. Accordingly, the pharmaceutical compositions disclosed herein may also contain one or more other active ingredients or therapeutic agents in addition to a compound disclosed herein, a combination regimen.

The particular combination of therapies (therapeutics or procedures) to employ in a combination regimen will take into account compatibility of the desired therapeutics and/or procedures and the desired therapeutic effect to be achieved. For example, other therapies that may be used in combination with the compounds of the disclosure include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and chemotherapeutic drugs.

In a particular embodiment, one or more compounds disclosed herein can be used in combination with one or more chemotherapeutic agents. Examples of chemotherapeutic agents include, but are not limited to, platinum analogs such as cisplatin and carboplatin; vinblastine; platinum; proteins such as arginine deiminase and asparaginase; alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL™, Bristol-Myers Squibb Oncology, Princeton, N.J.) and docetaxel (TAXOTERE™, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylomithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacyto sine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; and capecitabine.

The disclosure provides for the compounds disclosed herein to be administered in combination (e.g., simultaneously or sequentially) with other classes of compounds, including, but not limited to, sepsis treatments, such as drotrecogin-α; antibacterial agents, such as ampicillin; antifungal agents such as terbinafine; anticoagulants, such as bivalirudin; thrombolytics, such as streptokinase; non-steroidal anti-inflammatory agents, such as aspirin; antiplatelet agents, such as clopidogrel; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepam; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y (AC) antagonists (e.g., clopidogrel, ticlopidine and CS-747), and aspirin; anti-coagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP inhibitors; calcium channel blockers, such as amlodipine besylate; potassium channel activators; alpha-adrenergic agents; diuretics, such as chlorothlazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as *vinca* alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In further embodiments, the compounds disclosed herein can be used in vitro to study the effects of inhibiting immunoproteasomes in cells or used in biological/chemical assays in order to study the effects or consequences of down regulating the activity of immunoproteasomes on gene expression, protein processing, and the generation of peptides with a hydrophobic C terminus (i.e., peptides associated with antigen presentation).

In another embodiment, the disclosure provides a kit to conveniently and effectively carry out the methods in accordance with the disclosure. In general, the pharmaceutical pack or kit comprises one or more containers filled with one or more of the ingredients of the pharmaceutical compositions of the disclosure. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EXAMPLES

General.

All reagents were purchased from commercial sources and were used without further purification, unless otherwise stated. Chromatographic purification of products was accomplished using flash column chromatography with silica gel 60. All melting point data were measured on a Büchi Melting Point B-545 instrument and are uncorrected. IR spectra were obtained on a Perkin Elmer Spectrum One FT-IR spectrometer or a Bruker Alpha FT-IR spectrometer using the ATR accessory and are reported in absorption frequency (cm$^{-1}$). The specific rotation data were measured on a Rudolph Research Analytical AutoPol IV polarimeter. Proton ($^1$H) and carbon ($^{13}$C) NMR spectra were obtained on Varian Inova 300 (300 MHz and 75 MHz, respectively), Varian Inova 400 (400 MHz and 101 MHz, respectively), Varian Inova 500 (500 MHz and 126 MHz, respectively), or Bruker Avance 700 (700 MHz) spectrometers as noted, and were internally referenced to residual deuterated solvent signals and reported in terms of chemical shift (6 ppm). Mass spectra were obtained on an Agilent G3250AA LCMS instrument, using the criteria provided by Baell & Holloway. All tested compounds exhibited >95% purity based on clean NMR spectra without extraneous peaks.

Thiasyrbactin Design Considerations.

The design of the thiasyrbactins described herein was based on a concise syringolin B analog synthesis method, a method which can be applied to any lysine analog. Presented herein, the method exploits the commercial compound β-aminoethylcysteine, or thialysine. The sulfur atom of the commercial compound was envisioned to provide a synthetic handle to enable late-stage strategies to enhance solubility. The macrodilactam can be accessed synthetically in only a few steps. The compounds prepared in this study are shown below:

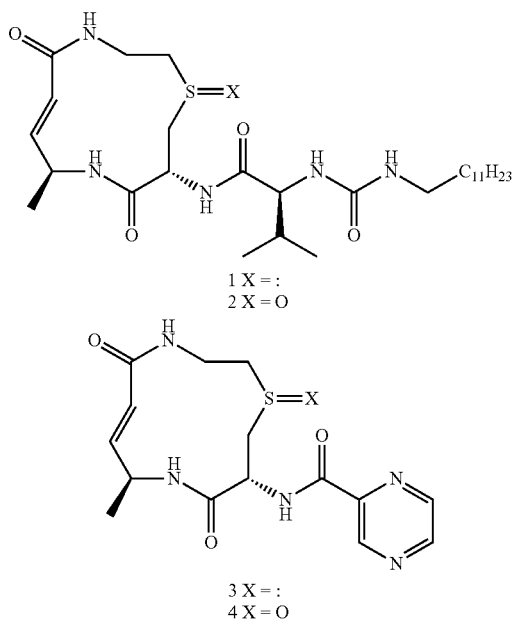

-continued

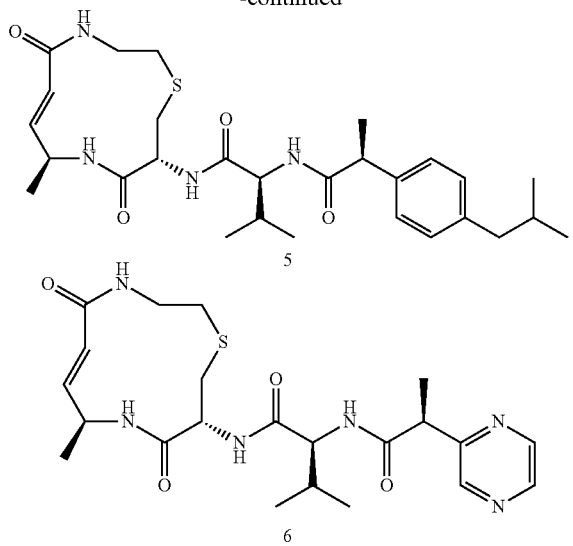

5

6

The same spatial relationship between the electrophilic carbon and the pyrazine seen in bortezomib is found in the unsaturated amide of 3 (NAM-41) and 4 (NAM-111). Compound 5 (NAM-93) retains the core of 1 (NAM-105) and 2 (NAM-135) but adds a branched, saturated, chiral carbon in the side chain, one strategy recommended to enhance solubility. Compound 6 (NAM-95) likewise retains the macrolactam-valine but terminates it with the more polar pyrazinamide. All of the compounds were evaluated computationally for their physicochemical properties that affect drug-likeness. These results are summarized below in Table 2.

TABLE 2

Properties affecting thiasyrbactin drug-likeness including solubility, hydrophobicity, and molecular weight.

| Compound | NAM # | $M_r$ (Da) | log $P^a$ | Log $S^b$ | Log $S_w{}^a$ |
|---|---|---|---|---|---|
| TIR-199 | — | 533 | 5.95 | −4.51 | −5.91 |
| GIbA | — | 520 | 3.12 | −3.89 | −4.24 |
| 1 | 105 | 553 | 5.51 | −4.65 | −5.75 |
| 2 | 135 | 569 | 3.89 | −4.36 | −4.83 |
| 3 | 41 | 349 | −0.76 | −3.03 | −1.50 |
| 4 | 111 | 365 | −2.38 | −2.91 | −0.58 |
| 5 | 93 | 531 | 3.86 | −4.52 | −5.09 |
| 6 | 95 | 448 | −0.05 | −3.56 | −2.33 |

Synthesis.

[a] Calculated using the method in Lagorce et al., Nucleic Acids Res. 43:W200-W207 (2015)).
[b] Calculated using the method in Lusci et al., J. Chem. Inf. Model 53:1563-1575.

A core macrodilactam 11 is common to all of the targets prepared, and its synthesis is summarized in Scheme 1.

Scheme 1. Synthesis of key macrodilactam.

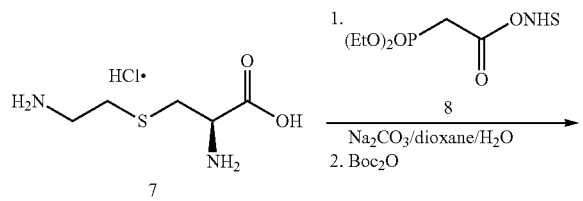

-continued

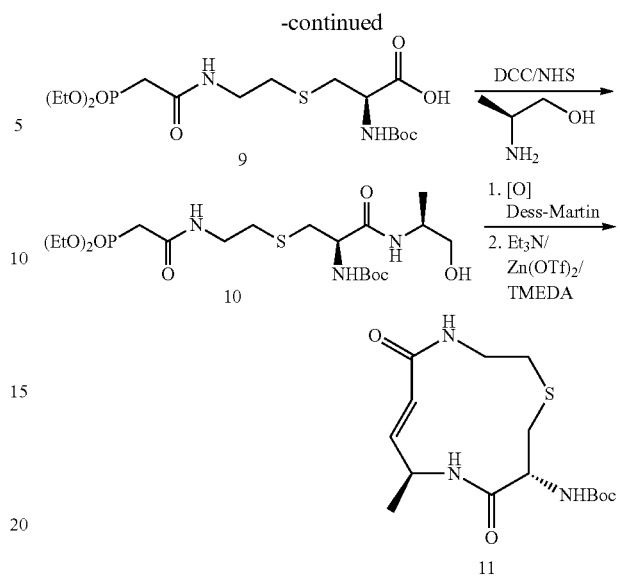

The commercial aminoethylcysteine hydrochloride (7, thialysine) was converted in one pot to the ε-phosphonoacetatamide/α-Boc derivative 9 in 83% yield. Small quantities of the doubly Boc-protected and α-phosphonoacetatamide/ε-Boc amino acids also resulted, their levels, however could be reduced using experimental optimization. Conventional carbodiimide coupling with alaninol gave 10 in 68% yield and set the stage for macrocycle formation. Dess-Martin oxidation of 10 gave an intermediate aldehyde that was not purified and was used directly in the next step. The Horner-Wadsworth-Emmons condensation process as modified by Helquist was applied to prepare dozens of macrolactam analogs in the syrbactin family. This is a highly reliable process resulted in superior yield when favorable conditions were utilized. Macrolactam 11 was afforded in 58% yield.

Stereochemical/Conformational Analysis of the Macrolactam.

The stereochemical/conformational analysis of the macrolactam was determined by using extensive proton NMR spectra of 11. Its C-2 and C-3 protons form an AA'BB' system and the C-11 and C-12 protons form an ABB' system. NMR data collected on 11 and 12 (vide infra) included high field proton, COSY and NOESY spectra. They are reported in Table 3. The three NH signals were not observed because spectra were taken in $d_4$-methanol.

TABLE 3

NMR Data for Macrolactams 11 and 12

| | | Compound 11 | | |
|---|---|---|---|---|
| Position | $\delta_C{}^a$ | $\delta_H{}^b$, mult. (J, Hz) | COSY | NOESY |
| 1-S | | | | |
| 2 | 32.4 | a: 2.47, m<br>b: 2.70, ddd (5.1, 8.6, 14.0) | 2b, 3a, 3b<br>2a, 3a, 3b$^d$ | 6 |
| 3 | 42.0 | a: 3.50, m<br>b: 3.22$^d$, m | 2a, 2b, 3b | 12a |
| 5 | 170.8 | | | |
| 6 | 121.3 | 6.45, d (15.7) | 7 | 2a, 12a |
| 7 | 146.0 | 6.72, dd (4.9, 15.6) | 6, 8 | |

TABLE 3-continued

NMR Data for Macrodilactams 11 and 12

| 8 | 48.0 | 4.52, m | 7, 8-Me | |
|---|---|---|---|---|
| 8-Me | 18.8 | 1.33, d (7.1) | | |
| 10 | 172.7 | | | |
| 11 | 53.8 | 4.43, m | 12a, 12b | |
| 12 | 34.1 | a: 3.00, dd (6.1, 14.4) | 11, 12b | 3a, 6 |
| | | b: 3.22$^d$, m | | |
| 2' | 157.2 | | | |
| 4' | 81.1 | | | |
| 5' | 28.8 | 1.45, s | 8 | |

Compound 12

| Position | $\delta_C{}^a$ | $\delta H^b$, mult. (J, Hz) | COSY | NOESY |
|---|---|---|---|---|
| 1-S | | | | |
| 2 | 54.5$^c$ | a: 3.29, m | 2b, 3a, 3b | 6 |
| | | b: 2.96, ddd (7.2, 8.9, 13.9) | 2a, 3a, 3b | |
| 3 | 37.4 | a: 3.70, m | 2a, 2b, 3b | 12a |
| | | b: 3.48, ddd (4.5, 6.9, 16.1) | 2a, 2b, 3a | 12b |
| 5 | 169.7 | | | |
| 6 | 120.0 | 6.15, d (15.4) | 7, 8 | 2a, 12a |
| 7 | 149.5 | 6.92, dd (4.8, 15.4) | 6, 8 | |
| 8 | 47.9 | 4.57, m | 6, 7, 8-Me | |
| 8-Me | 18.7 | 1.33, d (7.1) | 8 | |
| 10 | 170.9 | | | |
| 11 | 52.9 | 4.77, t (3.5) | 12a, 12b | |
| 12 | 54.5$^c$ | a: 3.14, dd (3.8, 14.4) | 11, 12b | 3a, 6 |
| | | b: 3.77, dd (3.2, 14.4) | 11, 12a | 3b |
| 2' | 157.1 | | | |
| 4' | 81.4 | | | |
| 5' | 28.8 | 1.45, s | 8 | |

$^a$Recorded at 126 MHz.
$^b$Recorded at 700 MHz.
$^c$The carbon signals 2 and 12 of compound 12 overlap.
$^d$The proton signals of 3b and 12b in compound 11 overlap.

Figure 3:
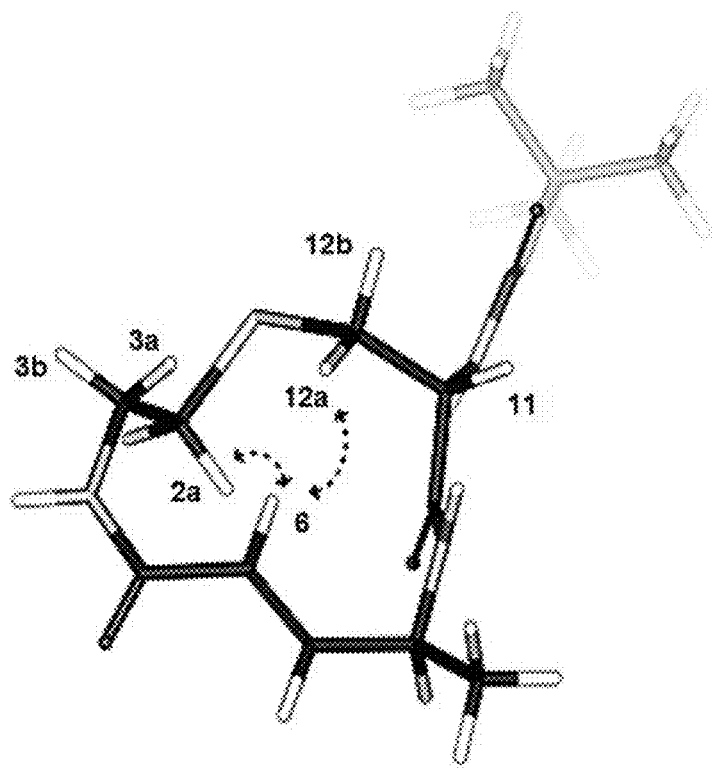
FIG. 3 demonstrates that the conformation of macrodilactam 11 is consistent with nOes and dihedral angles.

A conformational model of 11 was developed to aid in understanding 11's chemical and biological properties and to determine the configuration of the sulfoxide of 12. NOESY data were used to identify proximal transannular hydrogens that exerted substantial constraint on the available conformations. Based on molecular modeling, there are two main low-energy conformations available to 11, with the sulfide pointing above or below the nominal plane of the ring. The macrodilactam conformation observed (see FIG. 3) has the sulfide below the plane and has NOE correlations between H-6 and both H-2a and H-12a. The similar coupling constants between H-11 and both H-12a and H-12b in 11 further support this conformation. If the sulfide was pointing above the plane, the protons on C-12 would be pointed down, which would cause the dihedral angles between H-11 and H-12a/12b to be closer to 135°. This would result in a larger coupling constant than what was observed. Additionally, this structure would lack NOE correlations between the protons on C-3 and C-12.

Compound 11 was oxidized to sulfoxide 12, and was obtained as a single stereoisomer:

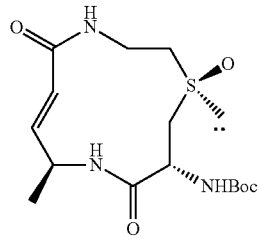

12

Figure 4:
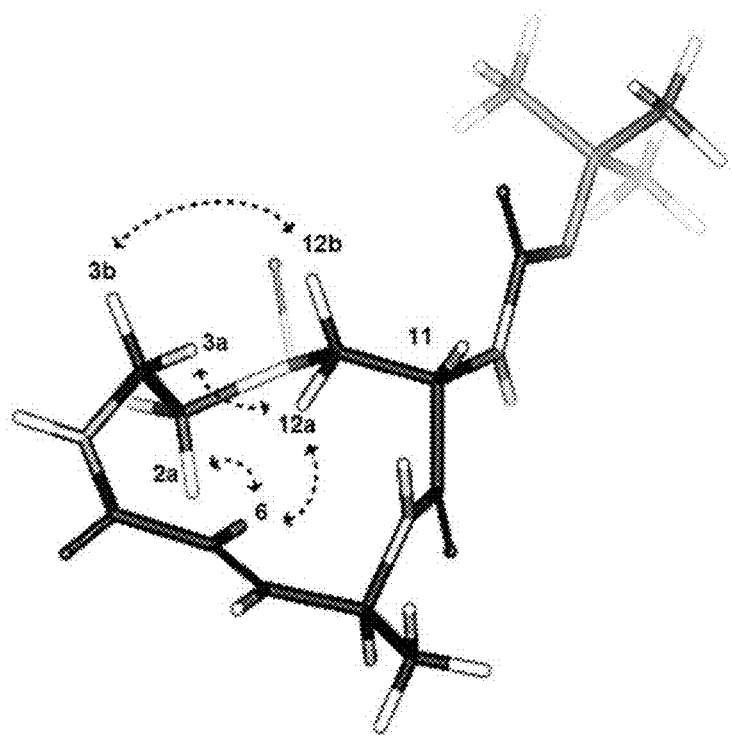
FIG. 4 demonstrates that the conformation of macrodilactam 12 consistent with nOes and dihedral angles.

The least hindered approach for the reactant would be from the equatorial direction to yield a beta sulfinyl group, an approach commonly seen with midsized rings. By analyzing 12's $^1$H NMR spectra, the conformation and sulfoxide configuration was confirmed (See FIG. 4). All adjacent protons were de-shielded in the sulfinyl derivative. The relationships among hydrogens, both in terms of dipolar and scalar couplings, are very similar to 11, supporting a similar conformation. Table 4 compares the modeled dihedral angles and those implied from J couplings.

TABLE 4

J-couplings for 12 with modeled and implied dihedral angles.

| Proton | δ (ppm) | J (Hz) | Θ (deg)$^a$ | Θ (deg)$^b$ |
|---|---|---|---|---|
| C2α | 3.29$^c$ | C2β | 108 | — |
| | | C3α | 68 | — |
| | | C3β | 156 | — |
| C2β | 2.96 | C2α-13.9 | gem | gem |
| | | C3α-8.9 | 168 | 170 |
| | | Cβ-7.2 | 32 | 20 |
| C3α | 3.70$^c$ | C3β | gem | gem |
| | | C2α | 68 | — |
| | | C2β | 168 | — |
| C3β | 3.48 | C3α-16.1 | gem | gem |
| | | C2α-6.9 | 156 | 150 |
| | | C2β-4.5 | 32 | 41 |
| C11 | 4.77 | C12α-3.5 | 48 | 47 |
| | | C12β-3.5 | 52 | 47 |
| C12α | 3.14 | C12β-14.4 | gem | gem |
| | | C11-3.8 | 48 | 45 |
| C12β | 3.77 | C12α-14.4 | gem | gem |
| | | C11-3.2 | 52 | 49 |

$^a$from modeled structure 11;
$^b$calculated from the Karplus equation;
$^c$multiplet Compound 12 showed additional NOE correlations between H-3b and H-12b, and H-3a and H-12a, strengthening the case for the 'sulfide below' conformation with slight inward rotation of C-3. The greatest de-shielding was experienced by H-2a, which has a dihedral angle with the sulfoxide of 162°. This relationship provided the greatest downfield shift when sulfides were converted to sulfoxides.

Continuing the synthesis from 11, the Boc group was removed with acid and the resulting hydrochloride salt was neutralized with a carbonate ion-exchange resin. The free base was then coupled with a valine active ester to provide 13. Removal of its Fmoc group and urea formation with dodecyl isocyanate provided the first target 1 (NAM-105). Periodate oxidation yielded the sulfoxide 2 (NAM-135) in a single stereoisomeric form, which based on spectral similarity to 12 and the precedent of its formation in the same type of reaction is assigned the beta configuration.

Scheme 2. Synthesis of thiasyrbactins 1 and 2

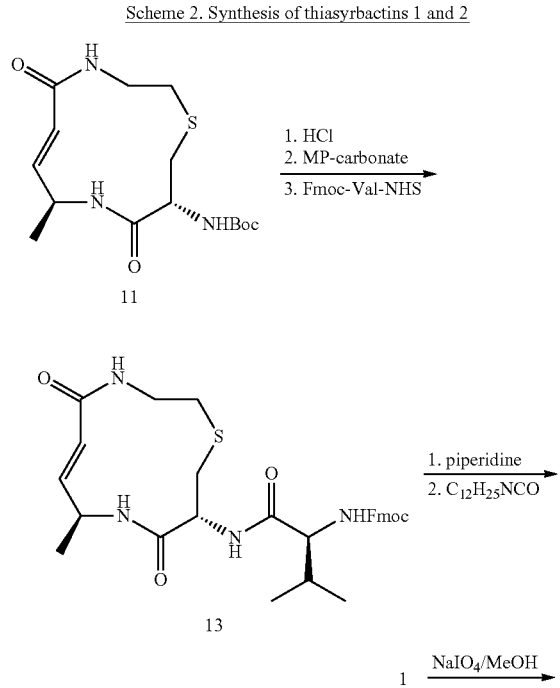

The other targets utilized active esters 14 and 15, which were prepared conventionally from the corresponding acids.

Chart 3. Side chain active esters.

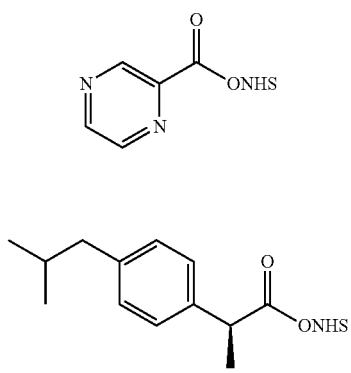

Macrolactam 11 was again deprotected and converted to the free base. It was coupled with pyrazine carboxylate to yield 3 (NAM-41) that was then oxidized to yield 4 (NAM-111) as a single stereoisomer. The $^1$H NMR properties of 4 (NAM-111) were very similar to those of 12, and therefore its sulfoxide configuration was likewise assigned the beta stereochemistry. Valine-substituted macrolactam 12 was the starting point for the preparation of 5 (NAM-93) and 6 (NAM-95) using straightforward methods.

Scheme 3. Synthesis of thiasyrbactins 3-6

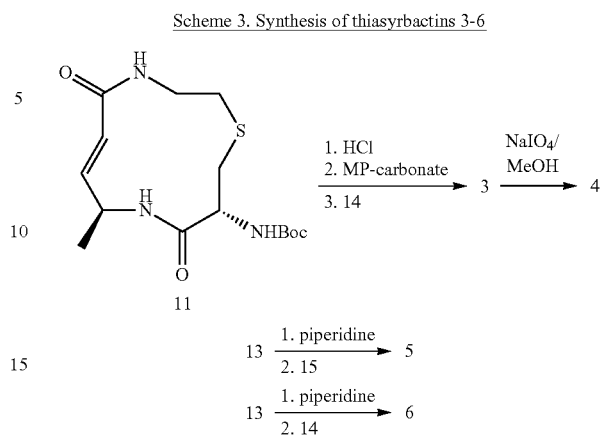

(S)-2-(3-Dodecylureido)-3-methyl-N-((8S,11R,E)-8-methyl-5,10-dioxo-1-thia-4,9-diazacyclo dodec-6-en-11-yl)butanamide 1 (NAM-105)

Compound 13 (19 mg, 33.6 μmol) was dissolved in dry dimethylformamide (1 mL) and treated with piperidine (6 μL). The solution was stirred for 40 min and the volatiles were removed in vacuo. After diluting the reaction mixture with dry dimethylformamide (1 mL), dodecylisocyanate (16 μL, 66.4 μmol) was added. The resulting mixture was stirred for 22 h at ambient temperature, and then concentrated in vacuo to obtain a solid that was purified by column chromatography (SiO$_2$, methanol/dichloromethane gradient, 0:10 to 1:9) to afford a white solid (0.0140 g, 75%). Mp: 231-233° C. [α]$^D_{25}$-28.4 (c 0.02, MeOH). IR (neat): 3311, 3270, 3064, 2958, 2923, 2853, 1626, 1544, 1466, 1386, 1283, 1239, 1219, 1168, 1095, 1017, 961, 915, 848, 721, 643 cm$^{-1}$. $^1$H NMR (400 MHz, CD3OD): δ 6.74 (dd, J=15.6, 4.8 Hz, 1H), 6.49 (d, J=15.6 Hz, 1H), 4.72-4.66 (m, 1H), 4.57-4.47 (m, 1H), 4.10 (d, J=5.3 Hz, 1H), 3.59-3.45 (m, 1H), 3.16-3.06 (m, 3H), 2.77-2.61 (m, 1H), 2.55-2.41 (m, 1H), 2.23-2.10 (m, 1H), 1.52-1.41 (m, 2H), 1.36-1.22 (m, 20H), 1.05-0.72 (m, 12H). $^{13}$C NMR (126 MHz, CD3OD): δ 145.9, 121.5, 78.4, 71.5, 60.7, 56.4, 53.0, 48.0, 41.8, 41.1, 33.9, 33.2, 32.7, 32.0, 31.4, 30.9, 30.6, 28.1, 23.9, 20.1, 18.8, 18.0, 14.6. HRMS calcd. for C$_{28}$H$_{52}$N$_5$O$_4$S [M+H]$^+$ 554.3740, found 554.3746.

(2S)-2-(3-Dodecylureido)-3-methyl-N-((8S,11R,E)-8-methyl-1-oxido-5,10-dioxo-1-thia-4,9-diazacyclododec-6-en-11-yl)butanamide 2 (NAM-135)

Compound 1 (12.7 mg, 22.9 μmol) was dissolved in methanol (1.5 mL) and stirred at 0° C. To which, a solution of sodium periodate (5.7 mg, 26.6 μmol) dissolved in water (0.2 mL) was added dropwise to form a reaction mixture. The reaction mixture was then stirred for 24 h and concentrated in vacuo. The crude solid was purified by column chromatography (SiO$_2$, methanol/dichloromethane gradient, 0:10 to 1:9) to give a white solid (7.8 mg, 60%). Mp: 204-206° C. [α]$^D_{25}$-36.3 (c 0.024, MeOH). IR (neat): 3316, 2956, 2921, 2852, 1708, 1657, 1622, 1553, 1522, 1457, 1377, 1340, 1293, 1238, 1205, 1166, 1091, 1042, 1013, 914, 853, 815, 766, 721, 648, 580, 541, 474, 456 cm$^{-1}$. $^1$H NMR (400 MHz, CD3OD): δ 6.87 (dd, J=15.3, 5.0 Hz, 1H), 6.16 (d, J=15.5 Hz, 1H), 4.97 (t, J=4.2 Hz, 1H), 4.57-4.33 (m, 1H), 4.08 (d, J=5.4 Hz, 1H), 3.76 (dd, J=14.6, 3.2 Hz, 1H), 3.71-3.64 (m, 1H), 3.49-3.42 (m, 1H), 3.17 (dd, J=14.4, 4.4 Hz, 1H), 3.09 (t, J=6.5 Hz, 1H), 2.97-2.88 (m, 1H), 2.19-2.12 (m, 1H), 1.47-1.42 (m, 2H), 1.39-1.12 (m, 22H), 1.06-0.73 (m, 12H). $^{13}$C NMR (126 MHz, CD3OD): δ 149.0, 120.2, 78.4, 60.6, 54.3, 54.1, 51.5, 47.9, 41.1, 37.2, 33.2, 32.0, 31.4, 30.9, 30.6, 28.1, 23.9, 20.1, 18.7, 18.0, 14.6. HRMS calcd. for $C_{28}H_{52}N_5O_5S$ [M+H]$^+$ 570.3689, found 570.3703.

N-((8S,11R,E)-8-Methyl-5,10-dioxo-1-thia-4,9-diazacyclododec-6-en-11-yl)pyrazine-2-carboxamide 3 (NAM-41)

The macrolactam 11 (60.1 mg, 0.175 mmol) was treated with hydrochloric acid in ethyl acetate (3 N, 2.0 mL) for 30 min under ambient temperature with stirring, and then concentrated in vacuo. The resulting hydrochloride salt was dissolved in dimethylformamide (2 mL). At 0° C., MP-carbonate resin (2.94 mmol/g, 0.1801 g, 0.529 mmol) was added followed by pyrazine carboxylic acid N-hydroxysuccinimide ester (14) (49.0 mg, 0.222 mmol). The resulting mixture was stirred at 0° C. for 15 min, 14 h at ambient temperature, and then concentrated in vacuo to obtain a crude solid that was further purified by column chromatography (SiO$_2$, methanol/dichloromethane gradient, 0:10 to 1:9) to afford a white solid (0.0293 g, 48%). Mp: 256-258° C. $[\alpha]^D_{25}$-13.9 (c 0.13, MeOH). IR (neat): 3450, 3387, 3374, 3265, 3044, 2986, 2932, 2918, 1721, 1684, 1666, 1651, 1628, 1582, 1543, 1514, 1464, 1454, 1404, 1364, 1350, 1335, 1308, 1293, 1268, 1241, 1218, 1167, 1156, 1094, 1047, 1021, 964, 947, 907, 893, 875, 852, 843, 795, 778, 734, 716, 688, 669 cm$^{-1}$. $^1$H NMR (300 MHz, CD3OD): δ 9.25 (d, J=1.4 Hz, 1H), 8.82 (d, J=2.5 Hz, 1H), 8.71 (dd, J=2.4, 1.5 Hz, 1H), 6.77 (dd, J=15.6, 4.9 Hz, 1H), 6.49 (d, J=15.7 Hz, 1H), 4.95 (dd, J=5.8, 1.9 Hz, 1H), 4.61-4.49 (m, 1H), 3.58 (ddd, J=14.7, 8.8, 4.1 Hz, 1H), 3.35 (d, J=2.8 Hz, 1H), 3.28-3.17 (m, 2H), 2.77 (ddd, J=14.4, 9.0, 5.1 Hz, 1H), 2.48 (ddd, J=14.9, 9.1, 6.0 Hz, 1H), 1.37 (d, J=7.1 Hz, 3H). $^{13}$C NMR (126 MHz, CD3OD): δ 171.7, 170.7, 164.3, 149.2, 146.0, 145.7, 145.1, 144.8, 121.2, 52.5, 48.1, 42.0, 33.7, 32.0, 18.8. HRMS calcd. for $C_{15}H_{20}N_5O_3S$ [M+H]$^+$ 350.1287, found 350.1298.

N-((8S,11R,E)-8-Methyl-1-oxido-5,10-dioxo-1-thia-4,9-diazacyclododec-6-en-11-yl)pyrazine-2-carboxamide 4 (NAM-111)

Compound 3 (6.2 mg, 17.7 μmol) was dissolved in methanol (1 mL) and stirred at 0° C. To which, a solution of sodium periodate (4.3 mg, 20.1 μmol) dissolved in water (0.2 mL) was added dropwise to form a reaction mixture. The reaction mixture was stirred for 24 hours and concentrated in vacuo. The white crude solid was purified by column chromatography (SiO$_2$, methanol/dichloromethane gradient, 0:10 to 1:9) to give a white solid (6.4 mg, 98%). Mp: 250-252° C. $[\alpha]^D_{25}$-32.0 (c 0.05, MeOH). IR (neat): 3370, 3332, 3267, 3067, 2956, 2922, 2852, 1674, 1661, 1646, 1629, 1583, 1529, 1472, 1454, 1407, 1366, 1354, 1282, 1267, 1238, 1213, 1169, 1155, 1091, 1050, 1021, 1006, 971, 945, 908, 883, 852, 775, 734, 717, 677, 631, 582, 553, 463, 432 cm$^{-1}$. $^1$H NMR (400 MHz, d$_6$-DMSO): δ 9.21 (s, 1H), 8.91 (d, J=2.1 Hz, 1H), 8.75 (d, J=7.5 Hz, 1H), 6.83 (dd, J=15.3, 4.6 Hz, 1H), 6.06 (d, J=15.0 Hz, 1H), 5.16 (dd, J=7.5, 3.6 Hz, 1H), 4.51 (dd, J=12.6, 7.3 Hz, 1H), 4.04-3.95 (m, 1H), 3.55-3.45 (m, 1H), 3.25-3.14 (m, 3H), 2.75-2.65 (m, 1H), 1.24 (d, J=6.4 Hz, 3H). $^{13}$C NMR (126 MHz, d$_6$-DMSO): δ 168.0, 165.5, 162.0, 148.2, 147.5, 143.7, 143.5, 143.3, 118.5, 55.3, 52.9, 50.5, 45.8, 36.5, 18.5. HRMS calcd. for $C_{15}H_{19}N_5O_4SNa$ [M+Na]$^+$ 388.1055, found 388.1040.

(S)-2-((S)-2-(4-Isobutylphenyl)propanamido)-3-methyl-N-((8S,11R,E)-8-methyl-5,10-dioxo-1-thia-4,9-diazacyclododec-6-en-11-yl)butanamide 5 (NAM-93)

Compound 13 (22.2 mg, 39.3 μmol) was dissolved in dry dimethylformamide (1 mL) and treated with piperidine (10 μL). The resulting solution was stirred for 30 min and volatiles were removed in vacuo. The residue was dissolved in dimethylformamide (1 mL) and (S)-(+)-ibuprofen N-hydroxysuccinimide ester (15) (27.8 mg, 91.6 μmol) was added. The resulting mixture was stirred at 0° C. for 30 min, 24 h at ambient temperature and concentrated in vacuo to obtain a crude white solid that was further purified by column chromatography (SiO$_2$, methanol/dichloromethane gradient, 0:10 to 1:9) to give a white solid (15.2 mg, 73%). Mp: 189-191° C. $[\alpha]^D_{25}$-37.1 (c 0.07, MeOH). IR (neat): 3274, 3055, 2957, 2925, 2870, 1706, 1630, 1535, 1459, 1382, 1282, 1220, 1166, 1088, 1030, 908, 848, 815, 777, 718, 659, 639, 577, 459 cm$^{-1}$. $^1$H NMR (300 MHz, CD3OD): δ 7.25 (d, J=8.1 Hz, 2H), 7.08 (d, J=7.9 Hz, 2H), 6.72 (dd, J=15.7, 4.9 Hz, 1H), 6.46 (d, J=15.4 Hz, 1H), 4.60 (dd, J=6.1, 1.9 Hz, 1H), 4.54-4.45 (m, 1H), 4.21 (d, J=7.4 Hz, 1H), 4.19-4.11 (m, 1H), 3.75 (dd, J=14.4, 7.2 Hz, 1H), 3.55-3.42 (m, 1H), 3.26-3.16 (m, 1H), 3.12 (dd, J=14.5, 2.2 Hz, 1H), 2.95 (dd, J=14.5, 6.2 Hz, 1H), 2.44 (d, J=7.1 Hz, 2H), 2.41-2.33 (m, 1H), 2.12-2.03 (m, 1H), 1.88-1.78 (m, 1H), 1.46 (d, J=7.1 Hz, 3H), 1.37-1.27 (m, 6H), 0.97-0.88 (m, 9H). $^{13}$C NMR (126 MHz, CD3OD): δ 177.7, 176.0, 173.1, 171.6, 170.9, 145.9, 141.6, 139.9, 130.5, 128.5, 121.5, 60.4, 53.1, 48.0, 47.0, 46.2, 42.0, 33.7, 32.7, 31.8, 31.6, 30.8, 30.1, 28.6, 26.4, 22.9, 19.9, 19.0, 18.8. HRMS calcd. for $C_{28}H_{42}N_4O_4SNa$ [M+Na]$^+$ 553.2825, found 553.2802.

N—((S)-3-Methyl-1-(((8S,11R,E)-8-methyl-5,10-dioxo-1-thia-4,9-diazacyclododec-6-en-11-yl)amino)-1-oxobutan-2-yl)pyrazine-2-carboxamide 6 (NAM-95). Compound 13 (59.7 mg, 0.106 mmol) was dissolved in dry dimethylformamide (2 mL) and treated with piperidine (20 μL). The solution was then stirred for 30 min and the volatiles were removed in vacuo. The residue was dissolved in dimethylformamide (2 mL) and then pyrazine carboxylic acid N-hydroxysuccinimide ester (14) (48.0 mg, 0.217 mmol) was added. The resulting mixture was stirred for 20 h at ambient temperature and concentrated in vacuo to obtain a crude solid that was further purified by column chromatography (SiO$_2$, methanol/dichloromethane gradient, 0:10 to 1:9) to give a white solid (19.8 mg, 42%). Mp: 241-243° C. $[\alpha]^D_{25}$-35.2 (c 0.05, MeOH). IR (neat): 3289, 3273, 3058, 2962, 2929, 2874, 1634, 1513, 1450, 1389, 1336, 1291, 1218, 1164, 1095, 1047, 1019, 961, 889, 859, 847, 775, 731, 645, 577, 439 cm$^{-1}$. $^1$H NMR (400 MHz, CD3OD): δ 9.24 (d, J=1.1 Hz, 1H), 8.81 (d, J=2.4 Hz, 1H), 8.71 (dd, J=2.3, 1.5 Hz, 1H), 6.72 (dd, J=15.6, 4.8 Hz, 2H), 6.49 (d, J=15.6 Hz, 1H), 4.71 (dd, J=19.0, 4.1 Hz, 1H), 4.59-4.55 (m, 1H), 4.51 (dd, J=13.9, 7.5 Hz, 1H), 3.55-3.46 (m, 1H), 3.27-3.16 (m, 2H), 3.05 (dd, J=14.3, 6.4 Hz, 2H), 2.73-2.65 (m, 1H), 2.54-2.45 (m, 1H), 2.30-2.18 (m, 1H), 1.33 (d, J=7.1 Hz, 3H), 1.05-0.99, m, 6H). $^{13}$C NMR (101 MHz, CD3OD): δ 173.7, 172.7, 171.7, 170.9, 165.1, 149.0, 145.9, 145.0, 121.5, 60.5, 59.9, 53.3, 53.1, 48.0, 41.9, 33.9, 32.8, 31.8, 29.7, 20.1, 19.9, 18.8. HRMS calcd. for $C_{20}H_{28}N_6O_4SNa$ [M+Na]$^+$ 471.1790, found 471.1796.

tert-Butyl ((S)-3-((2-(2-(diethoxyphosphoryl)acetamido)ethyl)thio)-1-(((S)-1-hydroxypropan-2-yl)amino)-1-oxopropan-2-yl)carbamate 10

L-4-Thialysine hydrochloride salt (7) (0.2965 g, 1.48 mmol) was dissolved in dioxane/water (1:1, 4 mL) and cooled to 0° C. Sodium carbonate (0.3149 g, 2.97 mmol) was added to the mixture at 0° C. After 30 min, phosphonoacetic acid N-hydroxysuccinimide ester (8) (0.4352 g, 1.48 mmol) was added. The mixture was stirred for 1 h at 0° C. and for 5 days at ambient temperature. A solution of Boc anhydride (0.6058 g, 2.78 mmol) dissolved in a minimum amount of dioxane was added drop-wise to the reaction mixture. The reaction mixture was stirred for 20 h at ambient temperature. The reaction mixture was washed with ethyl acetate (10 mL) to remove organic impurities. The aqueous phase was acidified to pH 2 using 1N hydrochloric acid, and extracted with ethyl acetate (4×15 mL). The combined organic extract was dried over anhydrous magnesium sulfate and concentrated to afford 9 as a colorless oil. This compound was used in the subsequent step without further purification.

The crude material 9 (0.5112 g, 1.16 mmol) was dissolved in 11 mL dry dichloromethane and set to stir at 0° C. N,N-Dicyclohexylcarbodiimide (0.2904 g, 1.41 mmol) and N-hydroxysuccinimide (0.1347 g, 1.17 mmol) were added at 0° C., followed by L-alaninol (0.18 mL, 2.31 mmol). The mixture was stirred at 0° C. for 30 min, then for 20 h at ambient temperature. The N,N-dicyclohexylurea was filtered off. The filtrate was concentrated to afford a yellowish oil that was purified by column chromatography (SiO$_2$, acetone/dichloromethane gradient, 1:4 to 4:1) to afford the title compound 10 as a colorless oil (0.3987 g, 54%). $[\alpha]^D_{25}$-14.99 (c 1.0, MeOH). IR (neat): 3289, 3282, 2978, 2931, 2875, 1711, 1651, 1531, 1454, 1411, 1392, 1365, 1239, 1164, 1097, 1048, 1020, 968, 865, 839, 781 cm$^{-1}$. $^1$H NMR (300 MHz, CDCl$_3$): δ 7.81 (s, 1H), 7.57 (d, J=5.7 Hz, 1H), 5.59 (d, J=8.4 Hz, 1H), 4.37-4.24 (m, 1H), 4.20-4.07 (m, 4H), 4.05-3.96 (m, 1H), 3.66 (dd, J=11.4, 3.4 Hz, 2H), 3.48 (dd, J=11.1, 5.8 Hz, 1H), 3.27 (br s, 1H), 2.90-2.78 (m, 4H), 2.67-2.54 (m, 1H), 1.42 (s, 9H), 1.32 (q, J=7.0 Hz, 6H), 1.16 (d, J=6.8 Hz, 3H). $^{13}$C NMR (75 MHz, CDCl$_3$): δ 170.7, 164.6, 155.9, 80.1, 66.1, 63.1, 62.9, 54.6, 47.9, 39.7, 36.7, 36.0, 34.3, 33.7, 28.4, 16.8, 16.5. HRMS calcd. for $C_{19}H_{39}N_3O_8PS$ [M+H]$^+$ 500.2195, found 500.2208.

tert-Butyl ((8S,11R,E)-8-methyl-5,10-dioxo-1-thia-4,9-diazacyclododec-6-en-11-yl) carbamate 11

Dess-Martin periodinane (0.4123 g, 0.972 mmol) was added to a stirring solution of phosphono-alcohol 10 (0.4051 g, 0.811 mmol) in dry dichloromethane (8 mL) at ambient temperature and stirred for 45 min. The reaction mixture was diluted with dichloromethane (12 mL) and 24 mL of a 1:1 mixture of sat NaHCO$_3$ and 2% sodium thiosulfate was added. The mixture was stirred vigorously until the organic phase became clear, then the phases were separated. The organic phase was dried over sodium sulfate, filtered, and concentrated in vacuo without warming to obtain a phosphono-aldehyde that was used without purification in the subsequent step.

Tetramethylethylenediamine (0.15 mL, 1.00 mmol) and triethylamine (0.46 mL, 3.30 mmol) were added to a stirred suspension of zinc triflate (0.6566 g, 1.81 mmol) in dry tetrahydrofuran (120 mL) at ambient temperature. The suspension was stirred for 45 minutes under an inert atmosphere. The crude phosphono-aldehyde was dissolved in dry tetrahydrofuran (70 mL) and added drop-wise to the suspension over 2.5 h. The reaction mixture was stirred at ambient temperature for 21 h and concentrated in vacuo to ca. 10 mL. The residue was diluted with ethyl acetate (100 mL) and washed with 50 mL each of brine and 1% hydrochloric acid. The organic phase was dried over magnesium sulfate and concentrated to afford a yellowish oil that was purified by chromatography (SiO$_2$, acetone/dichloromethane gradient, 1:4 to 4:1) to afford the title compound as a white solid film (0.1624 g, 58%). Mp: 176-179° C. $[\alpha]^D_{25}$-55.38 (c 0.30, MeOH). IR (neat): 3308, 2978, 2933, 1706, 1663, 1635, 1494, 1455, 1393, 1367, 1247, 1225, 1159, 1095, 1057, 1030, 974, 913, 885, 848, 759, 737 cm$^{-1}$. $^1$H NMR (700 MHz, CD3OD): δ 6.72 (dd, J=15.6, 4.9 Hz, 1H), 6.45 (d, J=15.6 Hz, 1H), 4.54-4.48 (m, 1H), 4.43 (d, J=4.4 Hz, 1H), 3.54-3.46 (m, 2H), 3.26-3.18 (m, 2H), 3.00 (dd, J=14.4, 6.1 Hz, 1H), 2.70 (ddd, J=14.0, 8.6, 5.8 Hz, 1H), 2.51-2.43 (m, 1H), 1.45 (s, 9H), 1.33 (d, J=7.1 Hz, 3H). $^{13}$C NMR (101 MHz, CD3OD): δ 172.7, 170.8, 157.2, 146.0, 121.3, 81.1, 53.8, 48.0, 42.0, 34.1, 32.4, 28.8, 18.8. HRMS calcd. for $C_{15}H_{26}N_3O_4S$ [M+H]$^+$ 344.1644, found 344.1650.

tert-Butyl ((8S,11R,E)-8-methyl-1-oxido-5,10-dioxo-1-thia-4,9-diazacyclododec-6-en-11-yl) carbamate 12

The macrolactam 11 (10.5 mg, 30.6 μmol) was dissolved in methanol (1 mL) and stirred at 0° C. To which, a solution of sodium periodate (8.2 mg, 38.3 μmol) dissolved in water (0.1 mL) was added drop-wise to form a reaction mixture. The reaction mixture was stirred for 24 hours and concentrated in vacuo. The white crude solid was purified by column chromatography (SiO$_2$, 1:9 methanol/dichloromethane) to give a white solid (9.8 mg, 89%). Mp: decomposition at 210° C. $[\alpha]^D_{25}$-108.76 (c 0.3, MeOH). IR (neat): 3417, 3295, 3218, 3094, 2975, 2927, 2467, 2387, 2263, 2204, 1710, 1671, 1632, 1535, 1469, 1366, 1249, 1162, 1018, 986, 852, 789, 668, 637, 569, 514, 432 cm$^{-1}$. $^1$H NMR (700 MHz, CD3OD): δ 6.92 (dd, J=15.4, 4.8 Hz, 1H), 6.15 (d, J=15.4 Hz, 1H), 4.77 (t, J=3.5 Hz, 1H), 4.59-4.55 (m, 1H), 3.77 (dd, J=14.4, 3.2 Hz, 1H), 3.73-3.67 (m, 1H), 3.48 (ddd, J=16.1, 6.9, 4.5 Hz, 1H), 3.30-3.27 (m, 1H), 3.14 (dd, J=14.4, 3.8 Hz, 1H), 2.96 (ddd, J=13.9, 8.9, 7.2 Hz, 1H), 1.45 (s, 9H), 1.33 (d, J=7.1 Hz, 3H). $^{13}$C NMR (126 MHz, CD3OD): δ 171.0, 169.7, 157.1, 149.5, 120.0, 81.4, 54.5, 54.4, 52.9, 47.9, 37.4, 28.8, 18.7. HRMS calcd. for $C_{15}H_{26}N_3O_5S$ [M+H]$^+$ 360.1588, found 360.1596.

(9H-Fluoren-9-yl)methyl ((S)-3-methyl-1-(((8S,11R,E)-8-methyl-5,10-dioxo-1-thia-4,9-diaza cyclododec-6-en-11-yl)amino)-1-oxobutan-2-yl)carbamate 13

The macrolactam 11 (0.1231 g, 0.358 mmol) was treated with hydrochloric acid in ethyl acetate (3N, 3.0 mL) and stirred for 30 min at ambient temperature, then concentrated in vacuo. The resulting hydrochloride salt was dissolved in dry dimethylformamide (4 mL) and stirred at 0° C. MP-Carbonate resin (2.94 mmol/g, 0.3663 g, 1.08 mmol) was added, followed by N-Fmoc-L-valine N-hydroxysuccinimide ester (0.1952 g, 0.447 mmol). The reaction mixture was stirred for 30 min at 0° C., then 24 h at ambient temperature. The reaction mixture was concentrated in vacuo to obtain a crude white solid that was purified by column chromatography (SiO$_2$, methanol/dichloromethane gradient, 0:10 to 1:9) to afford a white solid (0.1217 g, 60%). Mp: 207-209° C. [α]$^D_{25}$-55.43 (c 0.05, MeOH). IR (neat): 3282, 3063, 2959, 2925, 2872, 2854, 2463, 2409, 2375, 2353, 2338, 1692, 1635, 1538, 1450, 1390, 1342, 1290, 1249, 1237, 1219, 1163, 1135, 1101, 1084, 1033, 992, 960, 852, 795, 758, 739, 730, 668 cm$^{-1}$. $^1$H NMR (400 MHz, CD3OD): δ 7.80 (d, J=7.5 Hz, 2H), 7.71-7.64 (m, 2H), 7.39 (t, J=7.4 Hz, 2H), 7.31 (t, J=7.3 Hz, 2H), 6.72 (dd, J=15.6, 4.9 Hz, 1H), 6.47 (d, J=15.8 Hz, 1H), 4.71 (d, J=5.1 Hz, 1H), 4.54-4.47 (m, 1H), 4.37 (t, J=7.1 Hz, 1H), 4.25 (t, J=6.8 Hz, 1H), 3.99 (d, J=6.7 Hz, 1H), 3.55-3.46 (m, 1H), 3.20 (d, J=14.9 Hz, 1H), 3.07 (dd, J=14.3, 6.1 Hz, 1H), 2.73-2.62 (m, 1H), 2.52-2.42 (m, 1H), 2.19-2.06 (m, 1H), 1.32 (d, J=7.0 Hz, 3H), 0.97-0.93 (m, 6H). $^{13}$C NMR (126 MHz, CD3OD): δ 146.0, 128.9, 128.4, 126.4, 121.1, 68.2, 62.0, 53.0, 48.0, 41.8, 33.8, 32.7, 31.8, 30.9, 19.9, 18.8. (Partial $^{13}$C NMR data due to lack of compound solubility.) HRMS calcd. for C$_{30}$H$_{37}$N$_4$O$_5$S [M+H]$^+$ 565.2485, found 565.2497.

General Procedure for Synthesizing NHS Esters.

The N-hydroxysuccinimide esters of pyrazinecarboxylic acid and (S)-(+)-ibuprofen were prepared by dissolving the starting acid (0.200 g, 1.0 equiv) in dry tetrahydrofuran. With stirring at 0° C., N-Hydroxysuccinimide (1.0 equiv) was added followed by N,N-dicyclohexylcarbodiimide (1.0 equiv). The mixture was warmed to ambient temperature and stirred for 24 h. The N,N-dicyclohexylurea was removed by filtration and the filtrate was concentrated to afford a solid that was purified by column chromatography.

2,5-Dioxopyrrolidin-1-yl pyrazine-2-carboxylate 14.

The crude white solid was purified by column chromatography (SiO$_2$, acetone/dichloromethane, 1:4) to give a white solid (0.2757 g, 77%). Mp: 161-164° C. $^1$H NMR (300 MHz, CDCl$_3$): δ 9.40 (d, J=1.4 Hz, 1H), 8.90 (d, J=2.3 Hz, 1H), 8.83 (dd, J=2.4, 1.5 Hz, 1H), 2.95 (s, 4H). $^{13}$C NMR (101 MHz, CDCl$_3$): δ 168.9, 159.6, 149.3, 147.1, 145.2, 140.2, 25.8. IR (neat): 3501, 3324, 3276, 3078, 2929, 2851, 1875, 1806, 1785, 1703, 1653, 1626, 1571, 1533, 1468, 1449, 1420, 1399, 1360, 1306, 1260, 1243, 1203, 1183, 1153, 1075, 1060, 1048, 1025, 1011, 995, 951, 892, 876, 853, 811, 782, 764, 713 cm$^{-1}$. HRMS calcd. for C$_9$H$_8$N$_3$O$_4$ [M+H]$^+$ 222.0509, found 222.0502.

2,5-Dioxopyrrolidin-1-yl (S)-2-(4-isobutylphenyl)propanoate 15

The crude white solid was purified by column chromatography (SiO$_2$, ethyl acetate/hexane gradient, 1:4 to 2:3) to afford a white solid (0.2742 g, 93%). Mp: 74-76° C. [α]$^D_{25}$ 60.2 (c 1.0, MeOH). $^1$H NMR (500 MHz, CDCl$_3$): δ 7.27 (d, J=8.0 Hz, 2H), 7.15 (d, J=7.9 Hz, 2H), 4.04 (q, J=7.2 Hz, 1H), 2.79 (s, 4H), 2.47 (d, J=7.2 Hz, 2H), 1.87 (dp, J=13.4, 6.7 Hz, 1H), 1.64 (d, J=7.2 Hz, 3H), 0.91 (d, J=6.6 Hz, 6H). $^{13}$C NMR (126 MHz, CDCl$_3$) δ 170.2, 169.2, 141.4, 135.6, 129.9, 129.7, 127.5, 127.3, 45.2, 42.8, 42.7, 30.3, 25.8, 22.6, 19.2, 19.1. IR (neat): 3054, 2959, 2904, 2851, 1862, 1839, 1800, 1765, 1741, 1631, 1513, 1446, 1432, 1380, 1363, 1342, 1313, 1261, 1238, 1207, 1182, 1144, 1088, 1047, 991, 962, 924, 871, 850, 814, 769, 728, 688, 669, 641, 560, 507, 464 cm$^{-1}$. HRMS calcd. for C$_{17}$H$_{21}$NO$_4$Na [M+Na]$^+$ 326.1368, found 326.1368.

In Vitro Proteasome Activity Assay.

To determine the anti-proteasome activity of the thiasyrbactins in the in vitro environment, three catalytic activities (β1, β2, β5) of the proteasome were measured as described in Ibarra-Rivera et al., Tetrahedron 67:9950-6 (2011)). Bortezomib (BTZ) (LC Laboratories, Woburn, Mass.) and the immunoproteasome inhibitor ONX-0914 (UBP Bio, Aurora, Colo.) were used as controls. Purified 20S constitutive proteasome from human erythrocytes or immunoproteasome from human peripheral blood mononuclear cells (PBMCs) (Boston Biochem, Cambridge, Mass.) and luminogenic substrates Z-LRR-Glo, Z-nLPnLD-Glo, and Suc-LLVY-Glo (Promega, Fitchburg, Wis.) specific for the β1, β2, and β5 (also referred to as T-L, C-L, and CT-L) catalytic subunit activities, respectively, were used. Briefly, 2.2 ng/μL of constitutive proteasome and immunoproteosome were incubated with increasing concentration of proteasome inhibitor (0 to 10 μM) in 10 mM HEPES, pH 7.3, for two hours at 37° C. Equal volume of the appropriate luminogenic substrate was added to each reaction and luminescence was measured 10 minutes later using a Multi-Mode Synergy (Biotek, Inc., Winooski, Vt.) plate reader. Assays were done in triplicate (n=3). The Ki-50 values for each catalytic activity were determined for each of the inhibitors using Graphpad Prism 5 software (La Jolla, Calif.) and averaged using Microsoft Excel (Redmond, Wash.).

Cell Viability Assay.

To determine the effect of the thiasyrbactins proteasome inhibitors on the viability of cancer cells, three different human neuroblastoma (NB) cell lines were used. BTZ was included as a control. SK—N—Be2c, SK—N—SH cells (ATCC, Manassas, Va.) and MYCN2 cells were plated overnight in RPMI media containing 10% heat-inactivated fetal bovine serum (FBS) (Invitrogen, Carlsbad, Calif., USA), supplemented with penicillin (100 U/ml) and streptomycin (100 μg/ml). Cells were cultured at 37° C. in a humidified atmosphere containing 5% CO2 and treated with 0.01, 0.1 and 1 μM proteasome inhibitor for 24 hours. Cell viability was determined using the Cell Titer 96 AQueous One Cell Proliferation Assay (Promega) reagent MTS by measuring absorbance at 490 nm using a Multi-Mode Synergy plate reader as Ibarra-Rivera et al. Assays were done in duplicate with triplicate wells of treatment per experiment (n=6). Data were expressed as the average cell viability relative to untreated control cells using Microsoft Excel™.

Biological Properties of the Thiasyrbactins.

The thiasyrbactins were evaluated for their ability to inhibit each of the catalytic subunits of the constitutive and immunoproteasomes as well as for cytotoxic activity against neuroblastoma cancer cells. To test the inhibitory activity of 1 (NAM-105), 5 (NAM-93), and 6 (NAM-95), an in vitro assay was performed to test the effect of the thiasyrbactins on the three sub-catalytic activities (i.e., the CT-L, C-L, and T-L activities) of the constitutive proteasome and the immunoproteasome (Table 5).

TABLE 5

In vitro effects of thiasyrbactins on sub-catalytic activities of the constitutive proteasome and the immunoproteasome.

| | Constitutive Proteasome | | Immunoproteasome | | |
|---|---|---|---|---|---|
| | Ki-50 (μM) | SD | Ki-50 (μM) | SD | |
| 1 | 0.28 | 0.07 | >10 | — | CT-L (β5) |
| | >10 | — | >10 | — | C-L (β1) |
| | 1.76 | 0.78 | 1.39 | 0.11 | T-L (β2) |
| 5 | 0.91 | 0.18 | >10 | — | CT-L (β5) |
| | >10 | — | >10 | — | C-L (β1) |
| | 1.07 | 0.19 | 0.74 | 0.06 | T-L (β2) |

TABLE 5-continued

In vitro effects of thiasyrbactins on sub-catalytic activities of the constitutive proteasome and the immunoproteasome.

| | Constitutive Proteasome | | Immunoproteasome | | |
|---|---|---|---|---|---|
| | Ki-50 (μM) | SD | Ki-50 (μM) | SD | |
| 6 | 1.22 | 0.18 | >10 | — | CT-L (β5) |
| | >10 | — | >10 | — | C-L (β1) |
| | 0.92 | 0.12 | 0.75 | 0.03 | T-L (β2) |
| ONX-0914 | 0.56 | 0.19 | 0.11 | 0.02 | CT-L (β5) |
| | 2.07 | 0.30 | 1.32 | 0.21 | C-L (β1) |
| | 1.11 | 0.06 | 1.34 | 0.22 | T-L (β2) |
| BTZ | 0.01 | 0.00 | 0.01 | 0.00 | CT-L (β5) |
| | 0.02 | 0.00 | 0.03 | 0.01 | C-L (β1) |
| | 1.37 | 0.11 | 0.78 | 0.03 | T-L (β2) |

For a control comparison, the FDA-approved peptide boronic acid proteasome inhibitor bortezomib (BTZ) and the immunoproteasome inhibitor ONX-0914 (a peptide epoxyketone related to carfilzomib) were also tested using identical experimental conditions. While 1 (NAM-105), 5 (NAM-93), and 6 (NAM-95) predominantly inhibited the CT-L and T-L activities of the constitutive proteasome, the compounds selectively and more potently inhibited the T-L activity of the immunoproteasome. The compounds had no effect on CT-L or C-L activities. It was somewhat surprising that inhibition of the T-L activity by 5 (NAM-93) and 6 (NAM-95) appears to stimulate the CT-L activity of the immunoproteasome (see FIG. 5). In contrast, BTZ inhibits the CT-L and C-L sub-catalytic activities indiscriminately, with weaker activities against the T-L activity. The immunoproteasome inhibitor ONX-0914 exhibits higher potency against the immunoproteasome CT-L activity compared to the CT-L activity of the constitutive proteasome, but also inhibited the C-L and T-L activities of both proteasome types at higher concentrations. Thus, 1 (NAM-105), 5 (NAM-93), and 6 (NAM-95) more selectively target the T-L site with Ki-50 values at 1.39, 0.74, and 0.75 μM, respectively, and had no effect at ≤10 μM on the CT-L and T-L activities of the immunoproteasome.

Figure 6A:
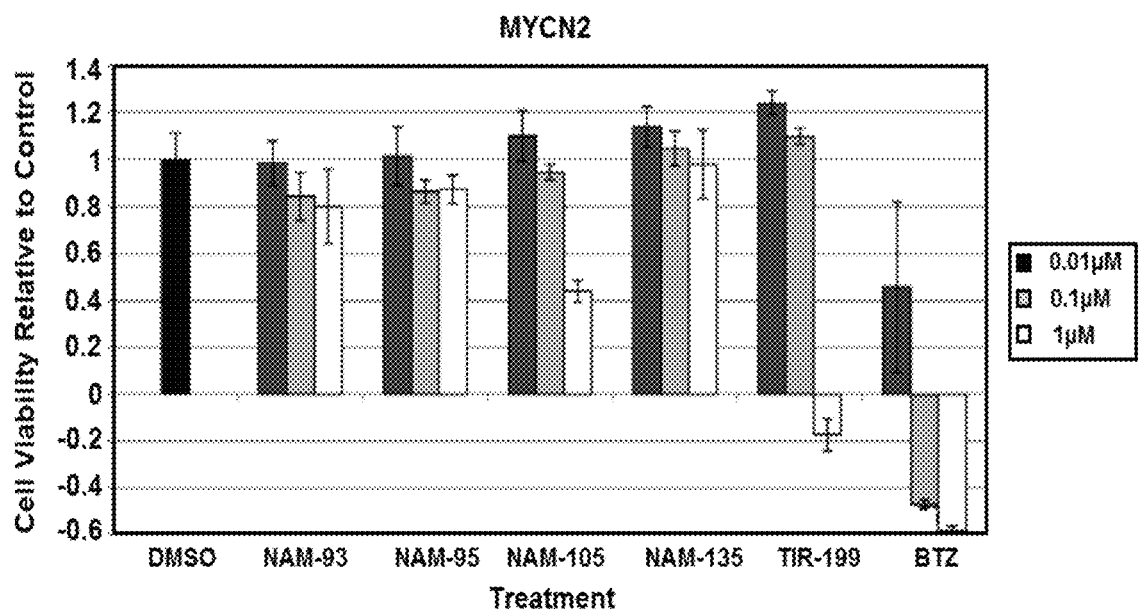
FIG. 6A-C demonstrates the effect of the compounds of the disclosure on the viability of human neuroblastoma cancer cells. (A) MYCN2, (B) SK—N—Be(2)c, and (C) SK—N—SH neuroblastoma cells were treated with 1 (NAM-105), 5 (NAM-93), or 6 (NAM-95) for 24 hours at three different concentrations (0.01, 0.1, and 1 µM). Bortezomib (BTZ) was included as a control. Cell viability was measured using the MTS reagent as described in the Methods section. Data shown are representative of two independent experiments, each performed in triplicate wells (n=6).
Figure 6B:
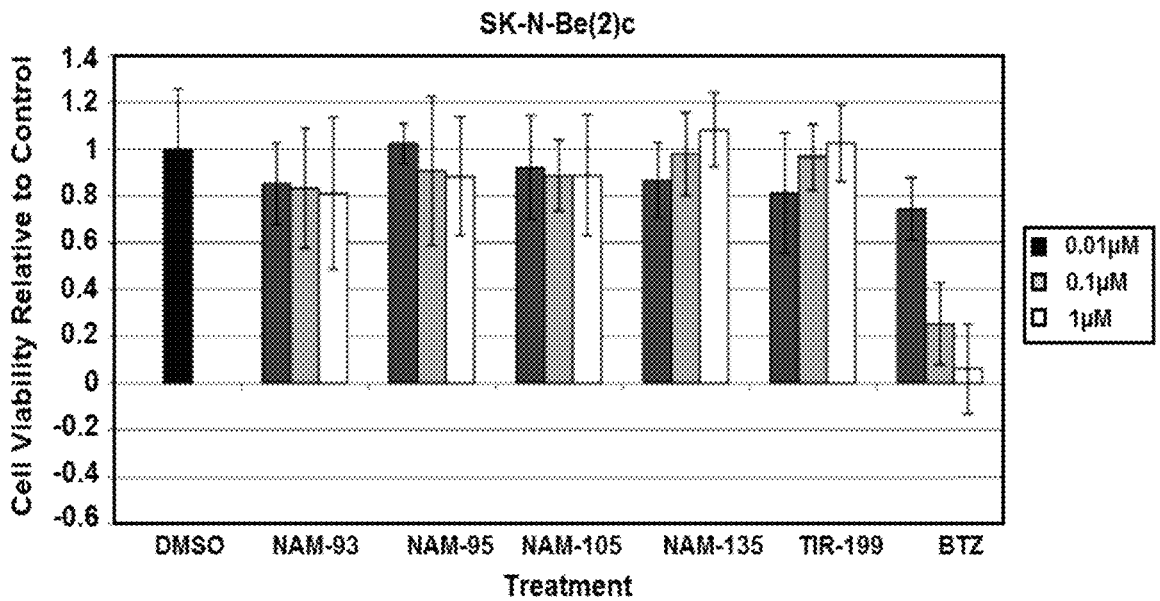
Figure 6C:
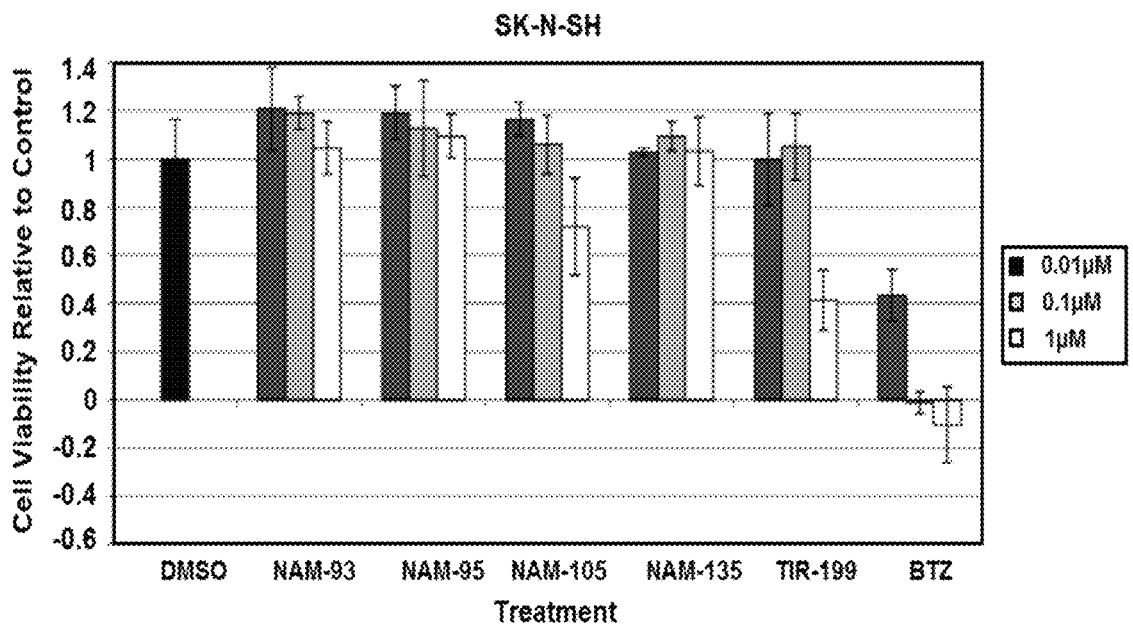
Figure 7A:
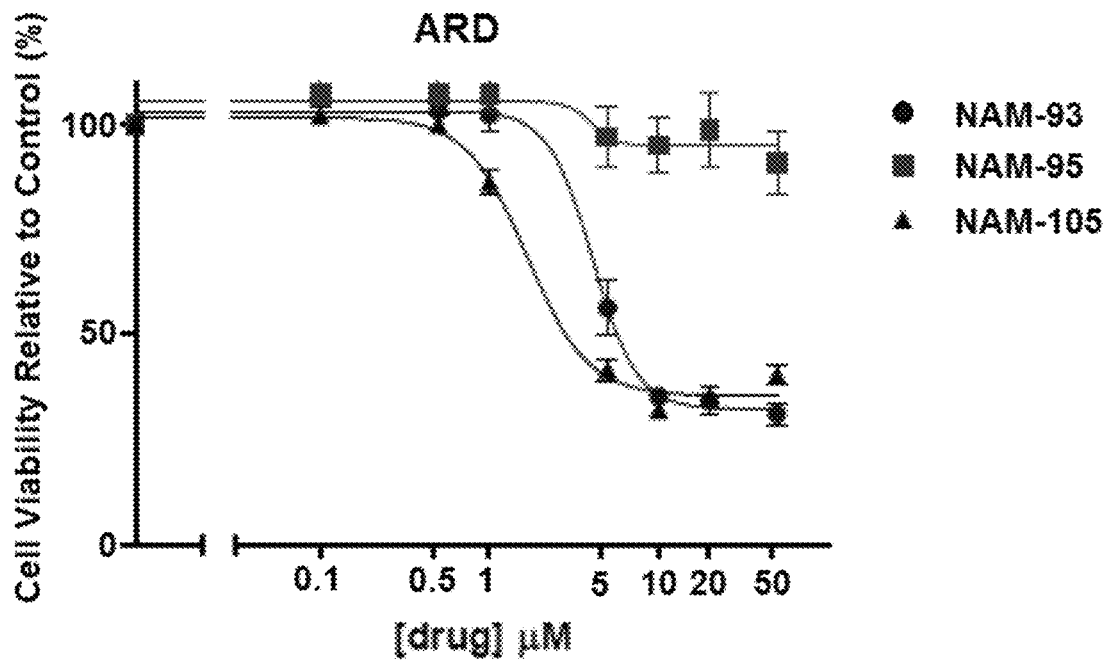
FIG. 7A-B demonstrates the dose dependent effect of the compounds of the disclosure on cell viability of human multiple myeloma (MM) cells (A) ARD and (B) U266. N=3. Cells were incubated for 24 hours in the presence of 1 (NAM-105), 5 (NAM-93), 6 (NAM-95) or DMSO (control) and cell viability measured using the MTS assay. IC-50s for ARD cells are 4.085±0.865 µM (5, NAM-93), N/A (6, NAM-95), and 1.673±0.337 µM (1, NAM-105). IC-50 for U266 cells are 3.308±0.916 µM (5, NAM-93), N/A (6, NAM-95), and 1.474±0.577 µM (1, NAM-105). N/A; not applicable (50% inhibition not reached at tested concentrations).
Figure 7B:
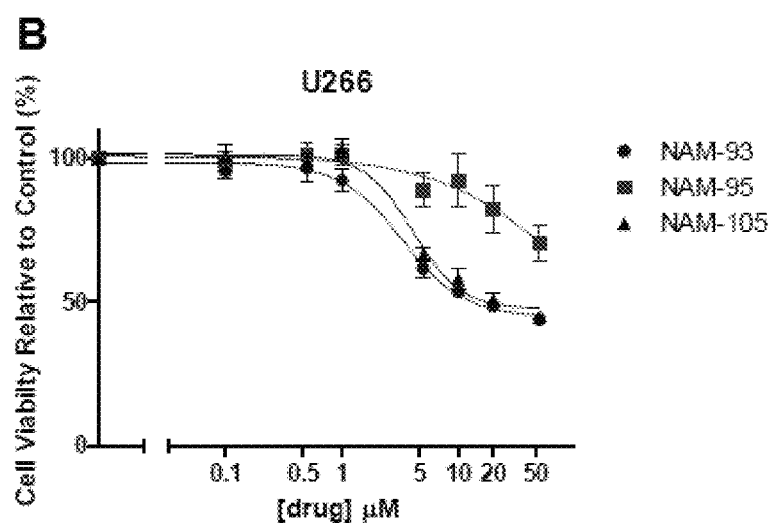

To study the biological effects of these thiasyrbactins, their action was tested on the viability of human neuroblastoma cells. As shown in FIG. 6A-C, thiasyrbactins 2 (NAM-135), 5 (NAM-93) and 6 (NAM-95) exhibited minimal effects on three neuroblastoma cell lines MYCN2, SK—N—Be(2)c, and SK—N—SH at the highest concentration tested (1 μM) after 24 hours exposure. In contrast, thiasyrbactin 1 (NAM-105) significantly inhibited the viability of MYCN2 and SK—N—SH cells at −30-50% of control (DMSO). TIR-199 strongly inhibits viability of MYCN2 and SK—N—SH cells as previously reported with little effect on SK—N—Be(2)c, a cell line originally derived from a highly metastatic, MYCN-amplified neuroblastoma tumor that exhibits chemoresistance. BTZ exhibits strong cytotoxic effects most prominently in MYCN2 and SK—N—SH cells at 0.1-1 μM.

A number of embodiments have been described herein. Nevertheless, it will be understood that various modifications may be made without departing from the spirit and scope of this disclosure. Accordingly, other embodiments are within the scope of the following claims.

What is claimed is:

1. A compound of Formula I:

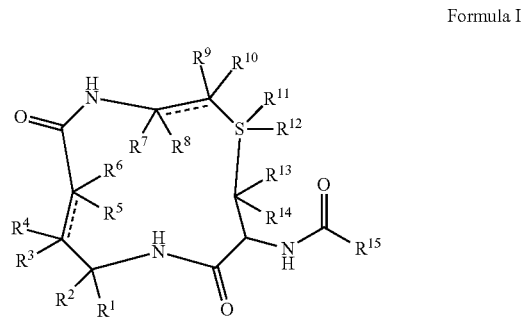

Formula I or a pharmaceutically acceptable salt, or solvate thereof, wherein, $R^1$ and $R^2$ are independently selected from the group consisting of H, cyano, an optionally substituted ($C_1$-$C_6$)alkyl and an optionally substituted cycloalkyl;

$R^3$-$R^{10}$, $R^{13}$ and $R^{14}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanate, isocyanato, an optionally substituted ($C_1$-$C_6$)alkyl, an optionally substituted ($C_2$-$C_6$)alkenyl, an optionally substituted ($C_2$-$C_6$)alkynyl, an optionally substituted ($C_1$-$C_6$)hetero-alkyl, an optionally substituted ($C_2$-$C_6$)hetero-alkenyl, an optionally substituted ($C_2$-$C_6$)hetero-alkynyl, an optionally substituted ($C_3$-$C_8$)cycloalkyl, an optionally substituted aryl, and an optionally substituted heterocycle;

$R^{11}$ and $R^{12}$ are independently selected from H, =O, and an optionally substituted ($C_1$-$C_6$)alkyl, wherein $R^{11}$ and/or $R^{12}$ may also be absent;

$R^{15}$ is selected from the group consisting of an optionally substituted heterocycle, an optionally substituted aryl, an optionally substituted benzyl, and an optionally substituted ($C_3$-$C_8$)cycloalkyl, —$CH_2(R^{19})$, —$CH(R^{19})_2$, —$NH(R^{19})$ and —$N(R^{19})_2$;

$R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted ($C_1$-$C_6$) alkyl, an optionally substituted ($C_2$-$C_6$)alkenyl, an optionally substituted ($C_2$-$C_6$)alkynyl, an optionally substituted ($C_1$-$C_6$)hetero-alkyl, an optionally substituted ($C_2$-$C_6$)hetero-alkenyl, an optionally substituted ($C_2$-$C_6$)hetero-alkynyl, an optionally substituted ($C_3$-$C_8$)cycloalkyl, an optionally substituted aryl, and an optionally substituted heterocycle;

$R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted ($C_3$-$C_8$)cycloalkyl; and $R^{19}$ is selected from the group consisting of an optionally substituted ($C_3$-$C_{16}$) alkyl, an optionally substituted ($C_3$-$C_{16}$)alkenyl, an optionally substituted ($C_3$-$C_{16}$) alkynyl, an optionally substituted ($C_3$-$C_{15}$)hetero-alkyl, an optionally substituted ($C_3$-$C_{15}$)hetero-alkenyl, an optionally substituted ($C_3$-$C_{15}$)hetero-alkynyl, an optionally substituted heterocycle, an optionally substituted aryl, an optionally substituted benzyl, and an optionally substituted ($C_3$-$C_8$)cycloalkyl.

2. The compound of claim 1 wherein the compound is Formula (II):

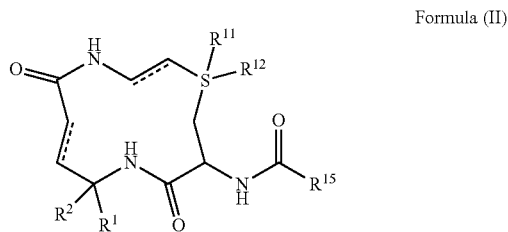

Formula (II)

or a pharmaceutically acceptable salt, or solvate thereof, wherein, $R^1$ and $R^2$ are independently selected from the group consisting of H, cyano, an optionally substituted ($C_1$-$C_6$)alkyl and an optionally substituted cycloalkyl;

$R^{11}$ and $R^{12}$ are independently selected from H, =O, and an optionally substituted ($C_1$-$C_6$)alkyl, wherein $R^{11}$ and/or $R^{12}$ may also be absent;

$R^{15}$ is selected from the group consisting of

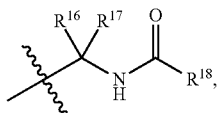

an optionally substituted heterocycle, an optionally substituted aryl, an optionally substituted benzyl, and an optionally substituted ($C_3$-$C_8$)cycloalkyl, —$CH_2(R^{19})$, —$CH(R^{19})_2$, —$NH(R^{19})$ and —$N(R^{19})_2$;

$R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted ($C_1$-$C_6$) alkyl, an optionally substituted ($C_2$-$C_6$)alkenyl, an optionally substituted ($C_2$-$C_6$)alkynyl, an optionally substituted ($C_1$-$C_6$)hetero-alkyl, an optionally substituted ($C_2$-$C_6$)hetero-alkenyl, an optionally substituted ($C_2$-$C_6$)hetero-alkynyl, an optionally substituted ($C_3$-$C_8$)cycloalkyl, an optionally substituted aryl, and an optionally substituted heterocycle;

$R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted ($C_3$-$C_8$)cycloalkyl, and $R^{19}$ is selected from the group consisting of an optionally substituted ($C_3$-$C_{16}$) alkyl, an optionally substituted ($C_3$-$C_{16}$)alkenyl, an optionally substituted ($C_3$-$C_{16}$) alkynyl, an optionally substituted ($C_3$-$C_{15}$)hetero-alkyl, an optionally substituted ($C_3$-$C_{15}$)hetero-alkenyl, an optionally substituted ($C_3$-$C_{15}$)hetero-alkynyl, an optionally substituted heterocycle, an optionally substituted aryl, an optionally substituted benzyl, and an optionally substituted ($C_3$-$C_8$)cycloalkyl.

3. The compound of claim 1, wherein the compound is Formula II(a):

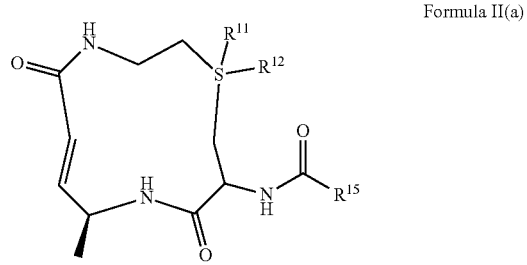

Formula II(a)

or a pharmaceutically acceptable salt, or solvate thereof, wherein, $R^{11}$ and $R^{12}$ are independently selected from H, =O, and an optional substituted ($C_1$-$C_6$)alkyl, or wherein $R^{11}$ and/or $R^{12}$ may also be absent;

$R^{15}$ is selected from the group consisting of

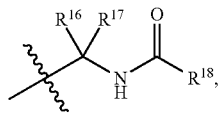

an optionally substituted heterocycle, an optionally substituted aryl, an optionally substituted benzyl, and an optionally substituted ($C_3$-$C_8$)cycloalkyl, —$CH_2(R^{19})$, —$CH(R^{19})_2$, —$NH(R^{19})$ and —$N(R^{19})_2$;

$R^{16}$ and $R^{17}$ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted ($C_1$-$C_6$) alkyl, an optionally substituted ($C_2$-$C_6$)alkenyl, an optionally substituted ($C_2$-$C_6$)alkynyl, an optionally substituted ($C_1$-$C_6$)hetero-alkyl, an optionally substituted ($C_2$-$C_6$)hetero-alkenyl, an optionally substituted ($C_2$-$C_6$)hetero-alkynyl, an optionally substituted ($C_3$-$C_8$)cycloalkyl, an optionally substituted aryl, and an optionally substituted heterocycle;

$R^{18}$ is selected from the group consisting of —$CH_2(R^{19})$, —$CH(R^{19})_2$, —$NH(R^{19})$, —$N(R^{19})_2$, an optionally substituted heterocycle, an optionally substituted aryl, an optionally substituted benzyl, and an optionally substituted ($C_3$-$C_8$)cycloalkyl; and $R^{19}$ is selected from the group consisting an optionally substituted ($C_3$-$C_{16}$) alkyl, an optionally substituted ($C_3$-$C_{16}$)alkenyl, an optionally substituted ($C_3$-$C_{16}$) alkynyl, an optionally substituted ($C_3$-$C_{15}$)hetero-alkyl, an optionally substituted ($C_3$-$C_{15}$)hetero-alkenyl, an optionally substituted ($C_3$-$C_{15}$)hetero-alkynyl, an optionally substituted heterocycle, an optionally substituted aryl, an optionally substituted benzyl, and an optionally substituted (C₃-C₈)cycloalkyl.

4. The compound of claim 1, wherein the compound is Formula II(b):

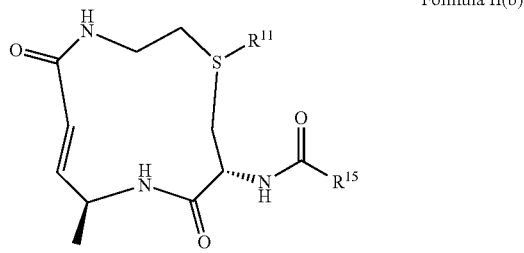

Formula II(b)

or a pharmaceutically acceptable salt, or solvate thereof, wherein,

R¹¹ is =O or is absent;

R¹⁵ is selected from the group consisting of

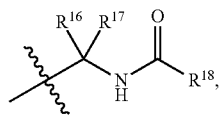

an optionally substituted heterocycle, an optionally substituted aryl, an optionally substituted benzyl, and an optionally substituted (C₃-C₈)cycloalkyl, —CH₂(R¹⁹), —CH(R¹⁹)₂, —NH(R¹⁹) and —N(R¹⁹)₂;

R¹⁶ and R¹⁷ are independently selected from the group consisting of H, halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted (C₁-C₆) alkyl, an optionally substituted (C₂-C₆)alkenyl, an optionally substituted (C₂-C₆)alkynyl, an optionally substituted (C₁-C₆)hetero-alkyl, an optionally substituted (C₂-C₆)hetero-alkenyl, an optionally substituted (C₂-C₆)hetero-alkynyl, an optionally substituted (C₃-C₈)cycloalkyl, an optionally substituted aryl, and an optionally substituted heterocycle;

R¹⁸ is selected from the group consisting of —CH₂(R¹⁹), —CH(R¹⁹)₂, —NH(R¹⁹), —N(R¹⁹)₂, an optionally substituted heterocycle, an optionally substituted aryl, an optionally substituted benzyl, and an optionally substituted (C₃-C₈)cycloalkyl, and R¹⁹ is selected from the group consisting of an optionally substituted (C₃-C₁₆) alkyl, an optionally substituted (C₃-C₁₆)alkenyl, an optionally substituted (C₃-C₁₆) alkynyl, an optionally substituted (C₃-C₁₅)hetero-alkyl, an optionally substituted (C₃-C₁₅)hetero-alkenyl, an optionally substituted (C₃-C₁₅)hetero-alkynyl, an optionally substituted heterocycle, an optionally substituted aryl, an optionally substituted benzyl, and an optionally substituted (C₃-C₈)cycloalkyl.

5. The compound of claim 1, wherein R¹⁵ is selected from the group consisting of:

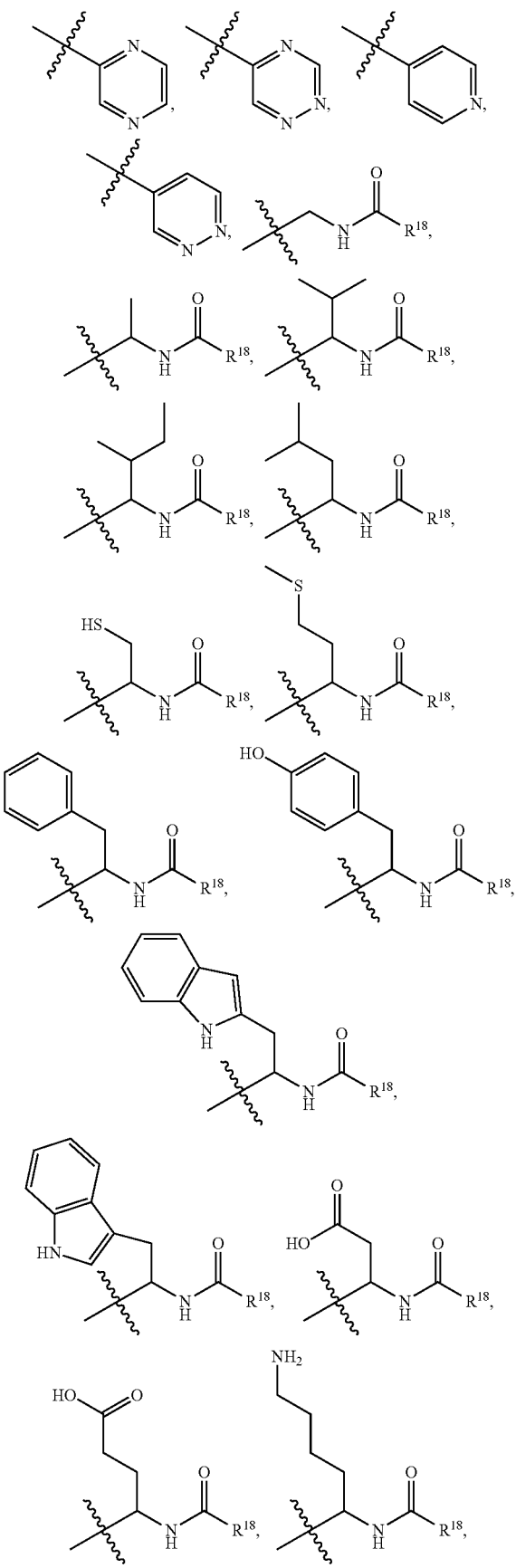

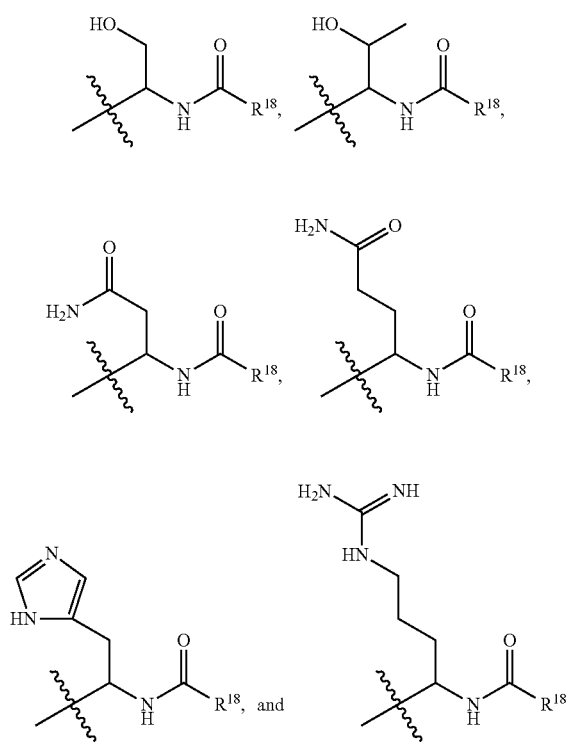

wherein,

R[18] is selected from the group consisting of —CH$_2$(R[19]), —CH(R[19])$_2$, —NH(R[19]), —N(R[19])$_2$, an optionally substituted heterocycle, an optionally substituted aryl, an optionally substituted benzyl, and an optionally substituted (C$_3$-C$_8$)cycloalkyl, and R[19] is selected from the group consisting an optionally substituted (C$_3$-C$_{16}$) alkyl, an optionally substituted (C$_3$-C$_{16}$)alkenyl, an optionally substituted (C$_3$-C$_{16}$) alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

6. The compound of claim 1, wherein the compound is Formula III:

Formula III

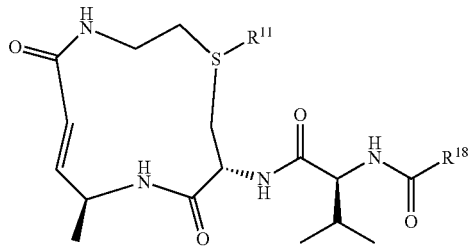

or a pharmaceutically acceptable salt, or solvate thereof, wherein,

R[11] is =O or is absent;

R[18] is selected from the group consisting of —CH$_2$(R[19]), —CH(R[19])$_2$, —NH(R[19]), —N(R[19])$_2$, an optionally substituted heterocycle, an optionally substituted aryl, an optionally substituted benzyl, and an optionally substituted (C$_3$-C$_8$)cycloalkyl, and R[19] is selected from the group consisting an optionally substituted (C$_3$-C$_{16}$) alkyl, an optionally substituted (C$_3$-C$_{16}$)alkenyl, an optionally substituted (C$_3$-C$_{16}$) alkynyl, an optionally substituted (C$_3$-C$_{15}$)hetero-alkyl, an optionally substituted (C$_3$-C$_{15}$)hetero-alkenyl, an optionally substituted (C$_3$-C$_{15}$)hetero-alkynyl, an optionally substituted heterocycle, an optionally substituted aryl, an optionally substituted benzyl, and an optionally substituted (C$_3$-C$_8$)cycloalkyl.

7. The compound of claim 1, wherein R[18] is selected from the group consisting of: octanyl, nonanyl, decanyl, undecanyl, dodecanyl, tridecanyl, tetradecanyl, pentadecanyl, hexadecnyl, octanyl, nonanyl, decanyl, undecanyl, dodecanyl, benzene, phenol, toluene, ethyl benzene, p-xylene, m-xylene, mesitylene, durene, 2-phyenylhexane, biphenyl, aniline, nitrobenzene, benzoic acid, naphthalene, anthracene, phenanthrene, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, quinolizidine and 1-ethyl-4-isobutyl benzene.

8. The compound of claim 1, wherein R[19] is selected from the group consisting of: octanyl, nonanyl, decanyl, undecanyl, dodecanyl, tridecanyl, tetradecanyl, pentadecanyl, hexadecnyl, benzene, phenol, toluene, ethyl benzene, p-xylene, m-xylene, mesitylene, durene, 2-phyenylhexane, biphenyl, aniline, nitrobenzene, benzoic acid, naphthalene, anthracene, phenanthrene, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, quinolizidine and 1-ethyl-4-isobutylbenzene.

9. The compound of claim 1, wherein the compound has the structure of:

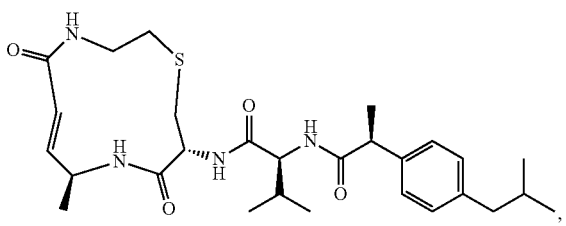 [SMILES: CC(C)Cc1ccc([C@H](C)C(=O)N[C@H](C(=O)N[C@H]2CSCCNC(=O)/C=C/[C@H](C)NC2=O)C(C)C)cc1]

or a pharmaceutically acceptable salt, or solvate thereof.

10. The compound of claim 1, wherein the compound has the structure of:

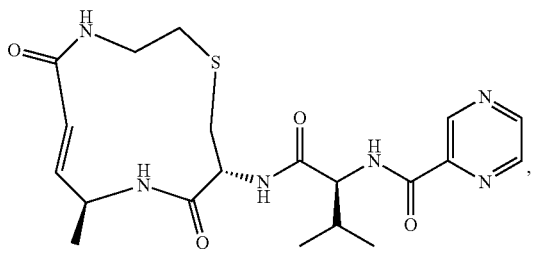 [SMILES: CC(C)[C@H](NC(=O)c1cnccn1)C(=O)N[C@H]1CSCCNC(=O)/C=C/[C@H](C)NC1=O]

or a pharmaceutically acceptable salt, or solvate thereof.

11. The compound of claim 1, wherein the compound has the structure of:

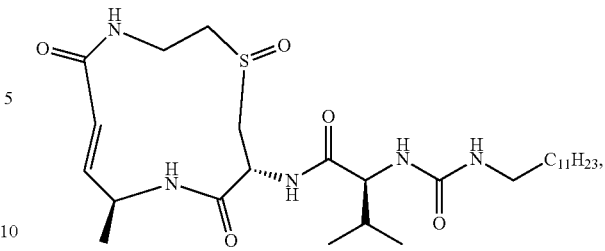

or a pharmaceutically acceptable salt, or solvate thereof.

12. A pharmaceutical composition comprising a compound of claim 1 and a pharmaceutically acceptable carrier.

13. The pharmaceutical composition of claim 12, wherein the composition is formulated to be administered intravenously, or subcutaneously.

14. A method of treating a subject having an immunoproteasome mediated disorder comprising administering a compound of claim 1, or a pharmaceutical composition containing the compound.

15. The method of claim 14, wherein the immunoproteasome mediated disorder is selected from the group consisting of an inflammatory disease, an autoimmune disease, obesity, and a metabolic disorder.

16. The method of claim 15, wherein the inflammatory disease is selected from the group consisting of colitis, asthma, inflammatory bowel disease, Crohn's disease, ulcerative colitis, Alzheimer's disease, and Nakajo-Nishimura syndrome.

17. The method of claim 15, wherein the autoimmune disease is selected from the group consisting of autoimmune encephalomyelitis, thyroiditis, rheumatoid arthritis, multiple sclerosis, systemic lupus erythematosus, Sjogren's syndrome, celiac sprue disease, pernicious anemia, vitiligo, scleroderma, psoriasis, Hashimoto's disease, Addison's disease, Graves' disease, and type 1 diabetes.

18. The method of claim 15, wherein the metabolic disorder is dyslipidemia or hyperglycemia.

19. The method of claim 14, wherein the immunoproteasome mediated disorder is a hematological malignancy.

20. The method of claim 19, wherein the hematological malignancy is multiple myeloma or mantle cell lymphoma.

* * * * *